United States Patent
Sato

(10) Patent No.: US 8,605,856 B1
(45) Date of Patent: Dec. 10, 2013

(54) RADIATION IMAGE CAPTURING DEVICE, RADIATION IMAGE CAPTURING SYSTEM, COMPUTER READABLE MEDIUM AND RADIATION IMAGE CAPTURING DEVICE CONTROL METHOD

(71) Applicant: Fujifilm Corporation, Tokyo (JP)

(72) Inventor: Keiichiro Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/960,195

(22) Filed: Aug. 6, 2013

Related U.S. Application Data

(62) Division of application No. 13/555,483, filed on Jul. 23, 2012, now Pat. No. 8,542,796.

(30) Foreign Application Priority Data

Aug. 31, 2011 (JP) .................................. 2011-189931
Apr. 3, 2012 (JP) .................................. 2012-084808

(51) Int. Cl.
  *G01T 1/17* (2006.01)
  *G01N 23/04* (2006.01)
(52) U.S. Cl.
  USPC ............................. 378/62; 250/394; 250/395
(58) Field of Classification Search
  USPC ............. 378/62, 98.8, 98.7, 98, 91; 250/394, 250/395
  See application file for complete search history.

(56) References Cited

U.S. PATENT DOCUMENTS

| 7,103,143 | B2 * | 9/2006 | Alving et al. ................ 378/98.7 |
| 7,573,979 | B2 | 8/2009 | Taoka et al. |
| 8,334,516 | B2 * | 12/2012 | Tsubota et al. .......... 250/370.08 |
| 2003/0086523 | A1 | 5/2003 | Tashiro et al. |
| 2003/0095629 | A1 * | 5/2003 | Nascetti et al. .............. 378/98.8 |
| 2003/0215058 | A1 | 11/2003 | Kinno et al. |
| 2005/0207533 | A1 * | 9/2005 | Nagai .......................... 378/98.8 |
| 2006/0065842 | A1 | 3/2006 | Okamura et al. |
| 2010/0148080 | A1 * | 6/2010 | Endo et al. ............... 250/370.08 |
| 2011/0019795 | A1 | 1/2011 | Fujita et al. |
| 2011/0176656 | A1 | 7/2011 | Kyushima et al. |

FOREIGN PATENT DOCUMENTS

| JP | 2004-24683 | 1/2004 |
| JP | 2006-246961 | 9/2006 |
| JP | 2009-153984 | 7/2009 |
| JP | 2009-195612 | 9/2009 |
| JP | 2010-264250 | 11/2010 |

* cited by examiner

*Primary Examiner* — Irakli Kiknadze
(74) *Attorney, Agent, or Firm* — Young & Thompson

(57) ABSTRACT

A radiation image capturing device is provided with plural pixels, a detection unit and a control unit. The pixels are each provided with a sensor portion and a switching element that reads out charges generated at the sensor portion and outputs the charges to a signal line. The detection unit detects the start of irradiation if electronic signals according to the charges satisfy a pre-specified condition for irradiation detection. After the start of irradiation of radiation is detected, the control unit acquires electronic signals corresponding to the charges and determines whether the acquired electronic signals include an electronic signal caused by noise. If the electronic signal caused by noise is included, the control unit controls a reporting unit so as to report this.

14 Claims, 32 Drawing Sheets

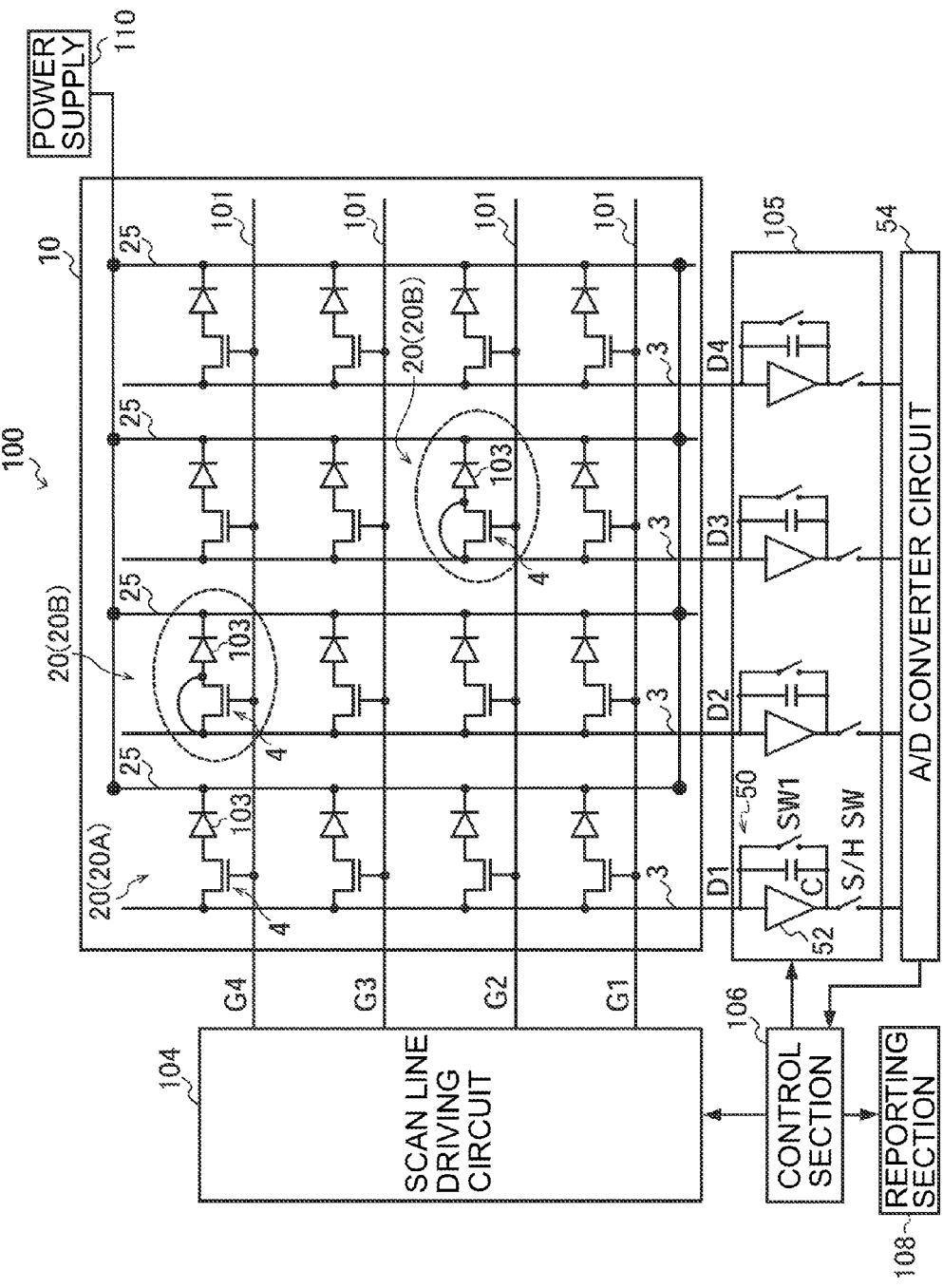

108 (LED)

108 (SPEAKER)

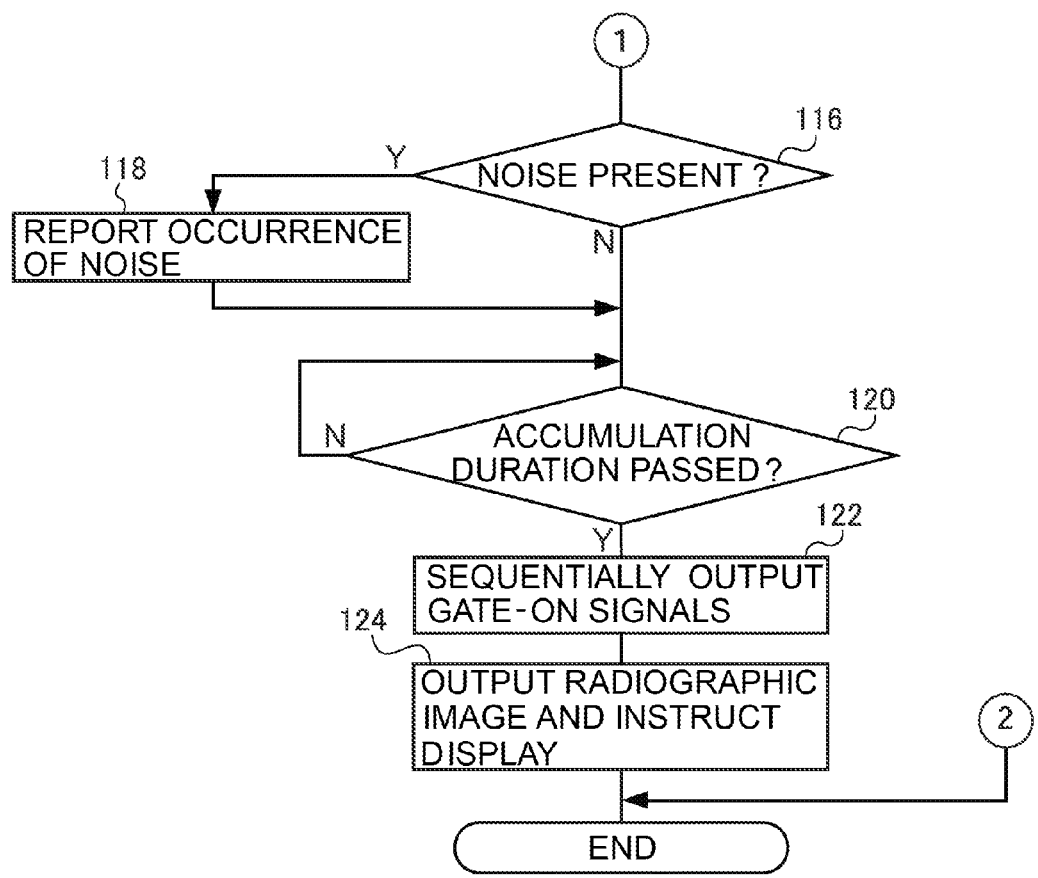

FIG.13

|   | SECOND THRESHOLD (+) | SECOND THRESHOLD (−) | THIRD THRESHOLD (+) | THIRD THRESHOLD (−) | RESULT |
|---|---|---|---|---|---|
| 1 | YES | NO | YES | NO | NO NOISE |
| 2 | YES | YES | YES | NO | WEAK NOISE |
| 3 | YES | YES | YES | YES | STRONG NOISE |

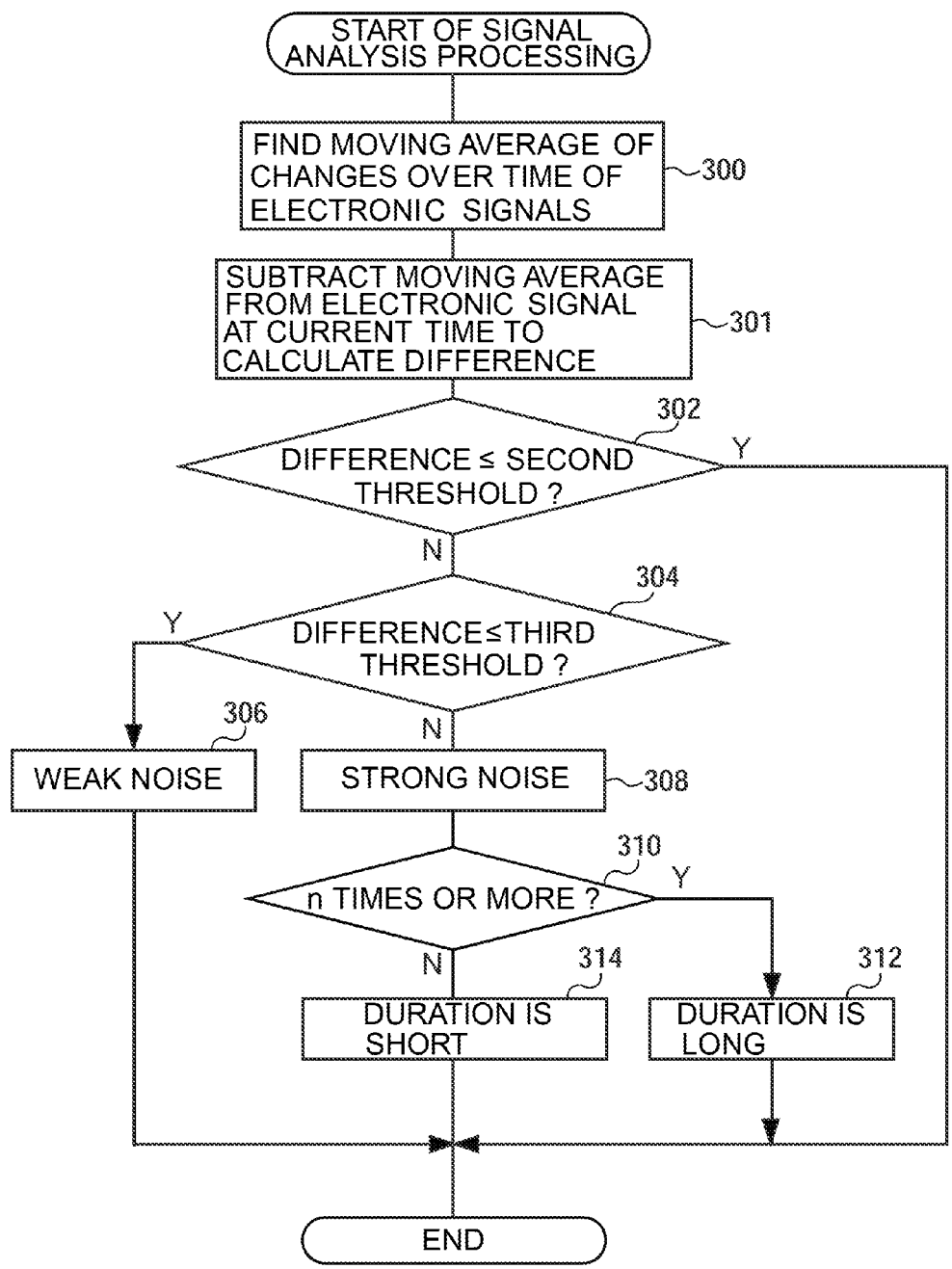

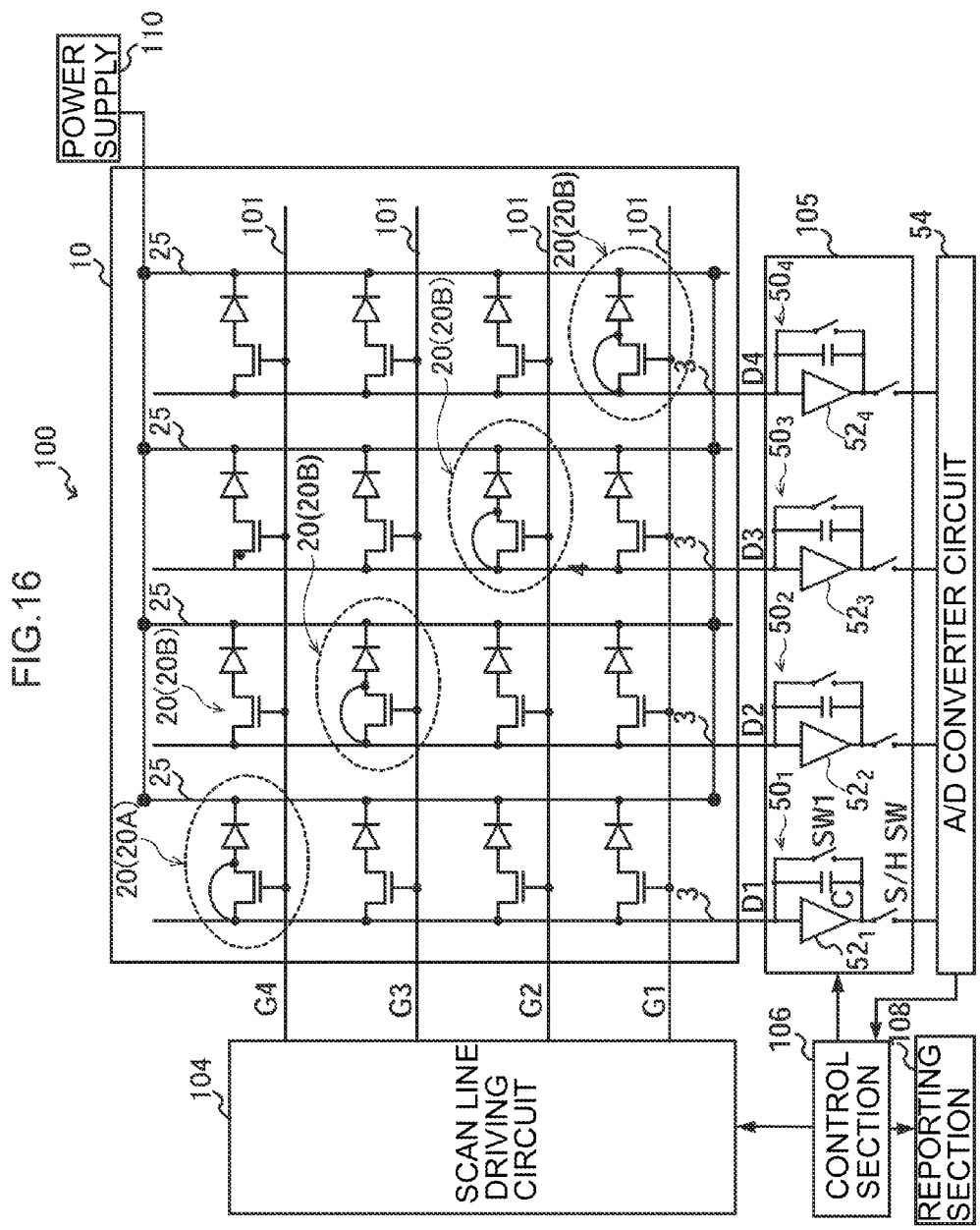

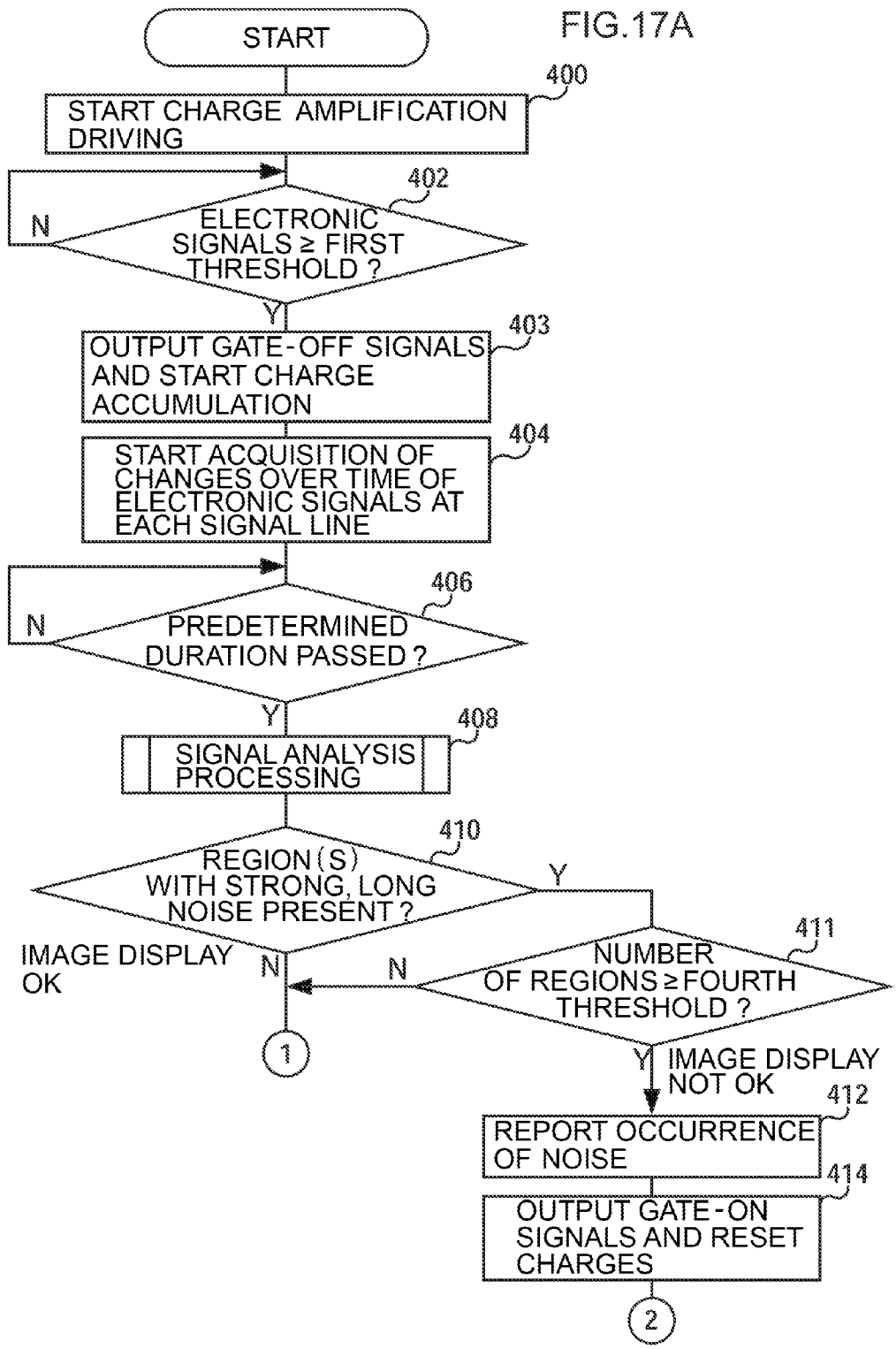

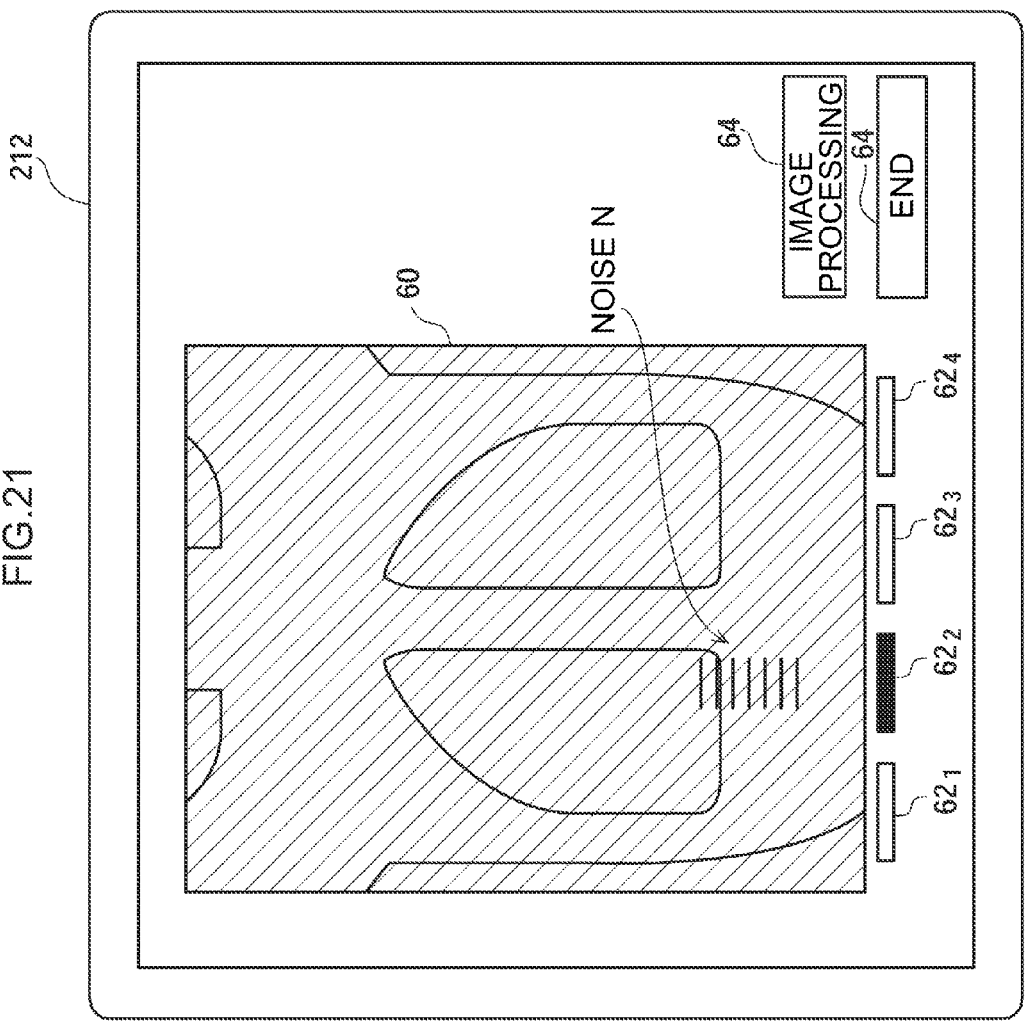

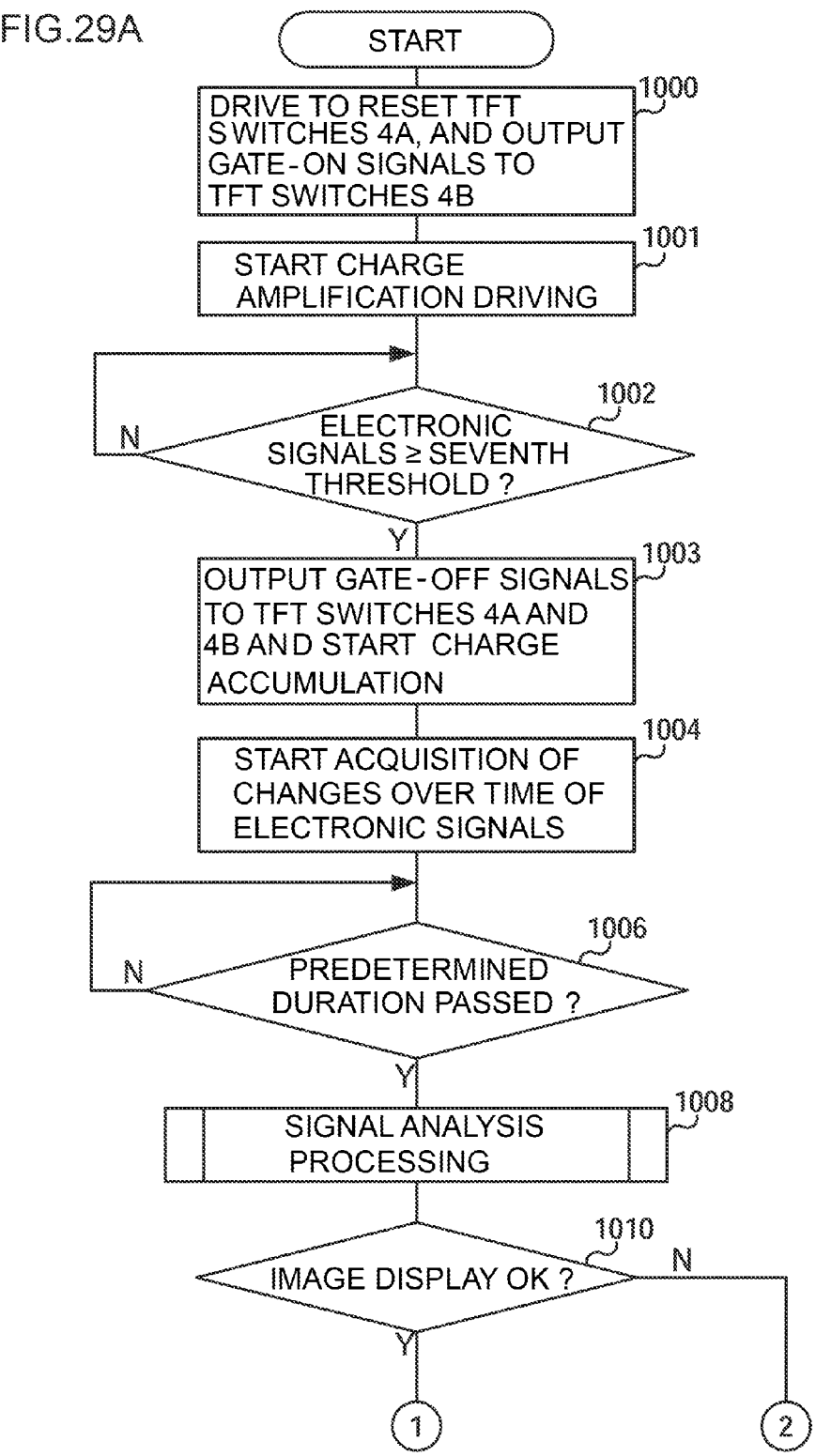

RADIATION IMAGE CAPTURING DEVICE, RADIATION IMAGE CAPTURING SYSTEM, COMPUTER READABLE MEDIUM AND RADIATION IMAGE CAPTURING DEVICE CONTROL METHOD

CROSS-REFERENCE TO RELATED APPLICATIONS

This application is a division of application Ser. No. 13/555,483 filed on Jul. 23, 2012, which claims priority under 35 USC 119 from Japanese Patent Application No. 2011-189931 filed on Aug. 31, 2011 and Japanese Patent Application No. 2012-084808 filed on Apr. 3, 2012, the disclosures of which are incorporated by reference herein.

BACKGROUND OF THE INVENTION

1. Field of the Invention

The present invention relates to a radiation image capturing device, a radiation image capturing system, a computer readable medium that stores a control program of the radiation image capturing device, and a control method of the radiation image capturing device, and particularly relates to a radiation image capturing device, a radiation image capturing system, a computer readable medium storing a control program of the radiation image capturing device, and a control method of the radiation image capturing device that are to be used for capturing radiographic images according to irradiated radiation.

2. Description of the Related Art

Heretofore, a radiation image capturing device that performs radiographic imaging for purposes of medical diagnostics and the like has been known. This radiation image capturing device detects radiation that has been irradiated from a radiation irradiation device and transmitted through an imaging subject, and captures a radiographic image. The radiation image capturing device captures a radiographic image by collecting and reading out charges that are generated in accordance with the irradiated radiation. A cassette or the like referred to as a flat panel detector (FPD panel) is mentioned as this kind of radiation image capturing device.

A radiation image capturing device is known that is equipped with: radiation detection elements formed of optoelectronic conversion elements or the like that generate charges in accordance with radiation, which is detected by the radiation, or light to which the radiation is converted, being irradiated thereon; switching elements that read out the charges generated by the radiation detection elements; and a detection section that detects an irradiation of radiation (the start, end and the like of the irradiation) on the basis of charges read out from the switching elements. For example, Japanese Patent Application Laid-Open (JP-A) No. 2010-264250 describes an x-ray imaging device that is provided with a reporting section that reports driving states of a detector that detects x-rays and makes synchronization with x-ray generation timings unnecessary.

In a case in which a radiographic image is captured by this kind of radiation image capturing device, electronic signals may be produced by external noise and the like, such as impacts, electromagnetic waves and the like, and anomalies may be produced by these electronic signals in the radiographic images that are captured.

Accordingly, there are technologies that detect the presence or absence of noise. For example, JP-A No. 2004-24683 describes a technology in which a noise detection section is provided separately from a radiation detection section (pixels) that detects radiation and, if it is determined on the basis of electronic signals that there is no noise, charges generated by the radiation detection section (pixels) are read out and a radiographic image is captured.

However, with the related art technologies described above, there is a concern that the presence or absence of noise may be misdetected if the timings of an occurrence of noise and an exposure of radiation are close together. In such a case, the occurrence of noise may not be appropriately reported to a user.

SUMMARY OF THE INVENTION

The present invention provides a radiation image capturing device, a radiation image capturing system, a radiation image capturing device, a computer readable medium that stores a control program of the radiation image capturing device, and a control method.

According to the first aspect of the present invention, there is provided a radiation image capturing device including: a plurality of pixels that are each provided with a sensor portion that generates a charge in accordance with an amount of radiation irradiated thereon, and a switching element that reads out the charge generated at the sensor portion and outputs the charge to a signal line; a detection unit that detects a start of irradiation if electronic signals corresponding to the charges generated at the sensor portions satisfy a pre-specified condition for irradiation detection; and a control unit that, after the start of an irradiation of radiation is detected by the detection unit, acquires electronic signals corresponding to the charges read out from the pixels, determines whether the acquired electronic signals include an electronic signal caused by noise, and, if an electronic signal caused by noise is included, controls a reporting unit so as to report the same.

According to the second aspect of the present invention, there is provided a radiation image capturing system including: a radiation irradiation device; and the radiation image capturing device according to the first aspect that captures a radiographic image according to radiation irradiated from the radiation irradiation device.

According to the third aspect of the present invention, there is provided there is provided a non-transitory computer readable medium storing a radiation image capturing device control program that causes a computer to execute a process for functioning as a control unit of a radiation image capturing device, the radiation image capturing device including: a plurality of pixels that are each provided with a sensor portion that generates a charge in accordance with radiation irradiated thereon, and a switching element that reads out the charge generated at the sensor portion and outputs the charge to a signal line; a detection unit that detects a start of irradiation of radiation if electronic signals corresponding to charges generated in the sensor portions satisfy a pre-specified condition for irradiation detection; and the control unit, which, after the start of irradiation of radiation is detected by the detection unit, acquires electronic signals corresponding to charges read out from the pixels, determines whether the acquired electronic signals include an electronic signal caused by noise, and, if an electronic signal caused by noise is included, controls a reporting unit so as to report the same.

According to the fourth aspect of the present invention, there is provided a radiation image capturing device control method including, when a radiographic image is being captured by a radiation image capturing device that includes a plurality of pixels that are each provided with a sensor portion that generates a charge in accordance with radiation irradiated thereon, and a switching element that reads out the charge generated at the sensor portion and outputs the charge to a signal line, detecting a start of irradiation of radiation if electronic signals corresponding to charges generated in the sensor portions satisfy a pre-specified condition for irradiation detection; after the start of irradiation of radiation is detected by the detecting, acquiring electronic signals corresponding to charges read out from the pixels; determining whether the acquired electronic signals include an electronic signal caused by noise; and, if an electronic signal caused by noise is included, controlling a reporting unit so as to report the same.

BRIEF DESCRIPTION OF THE DRAWINGS

Preferred embodiments of the present invention will be described in detail based on the following figures, wherein:

FIG. 2 is a structural diagram showing an example of overall structure of a radiographic image detector in accordance with the first exemplary embodiment.

FIGS. 7A and 7B are a flowchart of an example of radiation image capture processing in the radiation image capturing device in accordance with the first exemplary embodiment.

FIG. 13 is a descriptive diagram for describing a specific example of determinations of noise in the present exemplary equipment.

FIG. 14 is a flowchart of an example of signal analysis processing in the radiation image capturing device in accordance with the first exemplary embodiment.

FIG. 16 is a structural diagram showing an example of overall structure of a radiographic image detector in accordance with a third exemplary embodiment.

FIGS. 17A and 17B are a flowchart of an example of radiation image capture processing in a radiation image capturing device in accordance with the third exemplary embodiment.

FIG. 21 is a descriptive diagram for describing a specific example of display of a radiographic image in accordance with the third exemplary equipment.

FIGS. 29A and 29B are a flowchart of an example of radiation image capture processing in a radiation image capturing device in accordance with the seventh exemplary embodiment.

DETAILED DESCRIPTION OF THE INVENTION

Herebelow, an example of a present exemplary embodiment will be described while referring to the attached drawings.

First Exemplary Embodiment

Figure 1:
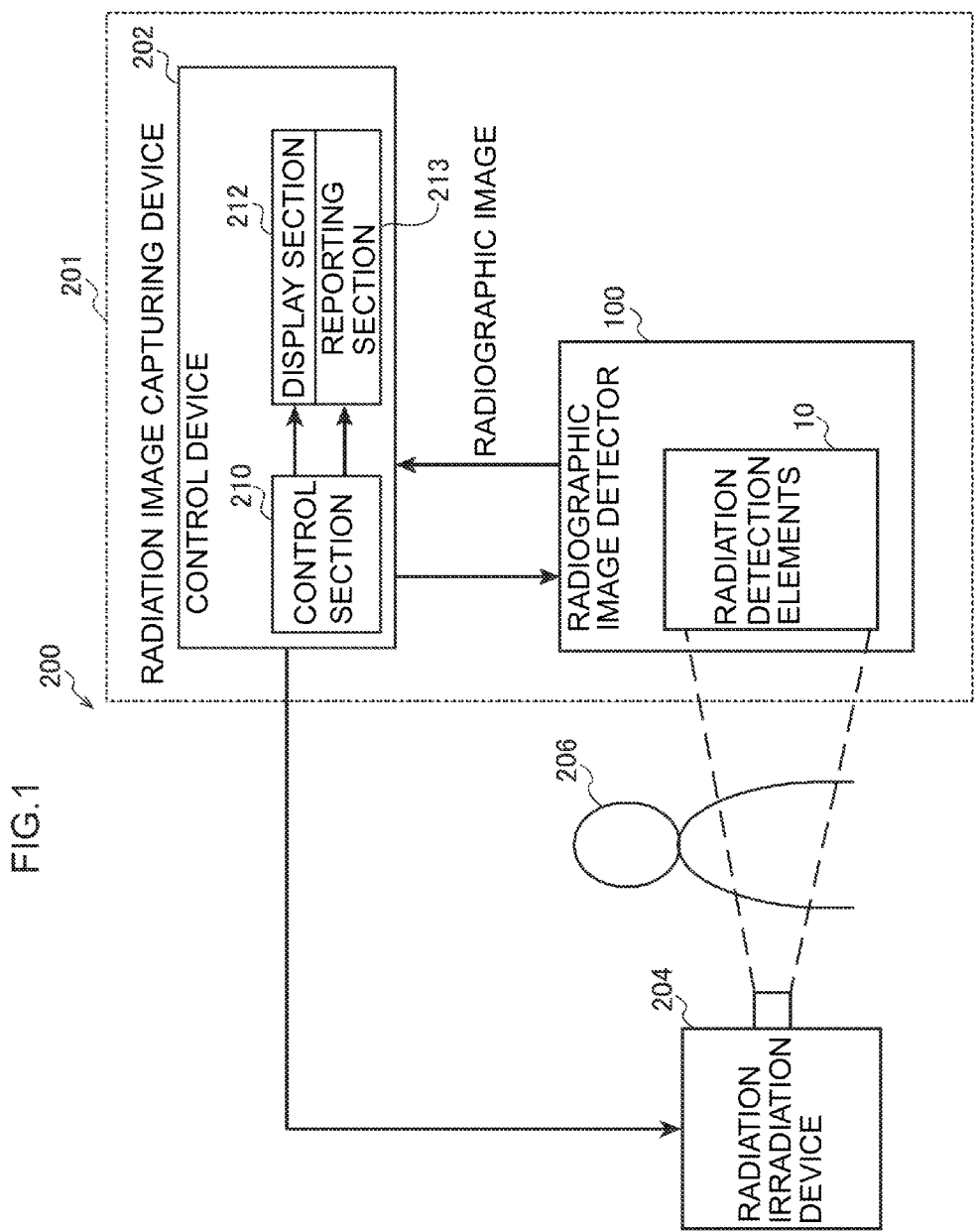
FIG. 1 is a schematic structural diagram showing general structure of an example of a radiation image capturing system in accordance with a first exemplary embodiment.

First, general structure of a radiation image capturing system that employs a radiation image capturing device of the present exemplary embodiment is described. FIG. 1 is a schematic structural diagram of an example of the radiation image capturing system of the present exemplary embodiment.

A radiation image capturing system 200 is provided with a radiation irradiation device 204, which irradiates radiation (for example, x-rays or the like) at an imaging subject 206, and a radiation image capturing device 201. The radiation image capturing device 201 is provided with a radiographic image detector 100, which is equipped with a radiation detector 10, and a control device 202. The radiation detector 10 detects radiation that has been irradiated from the radiation irradiation device 204 and transmitted through the imaging subject 206. The control device 202 instructs the capture of a radiographic image and acquires the radiographic image from the radiographic image detector 100. Radiation that is irradiated from the radiation irradiation device 204 at a timing in accordance with control by the control device 202 and transmitted through the imaging subject 206 disposed at an imaging position, and that carries image information, is irradiated at the radiographic image detector 100.

The control device 202 is provided with a control section 210, a display section 212 and a reporting section 213. The control section 210 includes functions for overall control of the control device 202 and the radiation image capturing device 201, and is constituted by a microcomputer. The control section 210 is provided with a central processing unit (CPU), ROM and RAM, and a non-volatile memory section constituted with flash memory or the like. The control section 210 executes a program memorized in the ROM with the CPU, and thus performs the above-mentioned control. The display section 212 is, for example, a display screen or a liquid crystal display or the like, and displays captured radiographic images. The display section 212 is not particularly limited, provided it has functions for displaying information relating to the capture of radiographic images and the like (including information relating to noise, which is described in detail below, and the like). The reporting section 213 includes functions for reporting to the user if noise at the radiographic image detector 100 is detected, which is described in detail below. Examples of the reporting section 213 include a speaker, a display device provided separately from the display section 212, light-emitting diodes and so forth, and the reporting section 213 is not particularly limited. In a case in which the control device 202 displays information relating to the detection of noise only at the display section 212, the reporting section 213 need not be provided.

Next, general structure of the radiographic image detector 100 of the present exemplary embodiment is described. A schematic diagram illustrating an example of overall structure of the radiographic image detector 100 according to the present exemplary embodiment is shown in FIG. 2. In the present exemplary embodiment, a case of application of the present invention to the radiographic detector 10 of an indirect conversion type, in which radiation of x-rays or the like is temporarily converted to light and the converted light is then converted to electric charges, is described. In the present exemplary embodiment, the radiographic image detector 100 is equipped with the indirect conversion-type radiation detector 10. A scintillator that converts the radiation to light is not shown in FIG. 2.

In the radiation detector 10, plural pixels 20 that each include a sensor portion 103 and a TFT switch 4 are arranged in a matrix pattern. The sensor portion 103 receives light and generates electric charges, and accumulates the generated charges. The TFT switch 4 is a switching element for reading out the charges accumulated in the sensor portion 103. In the present exemplary embodiment, the sensor portion 103 generates charges when irradiated with light converted by the scintillator.

The pixels 20 are plurally arranged in the matrix in one direction (the direction of the scan lines in FIG. 2, which is hereinafter referred to as the row direction), and a direction intersecting the row direction (the direction of the signal lines in FIG. 2, which is hereinafter referred to as the column direction). The arrangement of the pixels 20 is simplified in FIG. 2; for example, the pixels 20 are arranged in 1,024 rows by 1,024 columns.

In the present exemplary embodiment, among the plural pixels 20, radiation image capturing pixels 20A and radiation detection pixels 20B are specified in advance. In FIG. 2, the radiation detection pixels 20B are encircled by broken lines. The radiation image capturing pixels 20A are used for detecting radiation and generating an image representing the radiation. The radiation detection pixels 20B are pixels that are used for detecting radiation, and output charges regardless of the TFT switches 4 being turned on and off (described in detail below).

Figure 4:
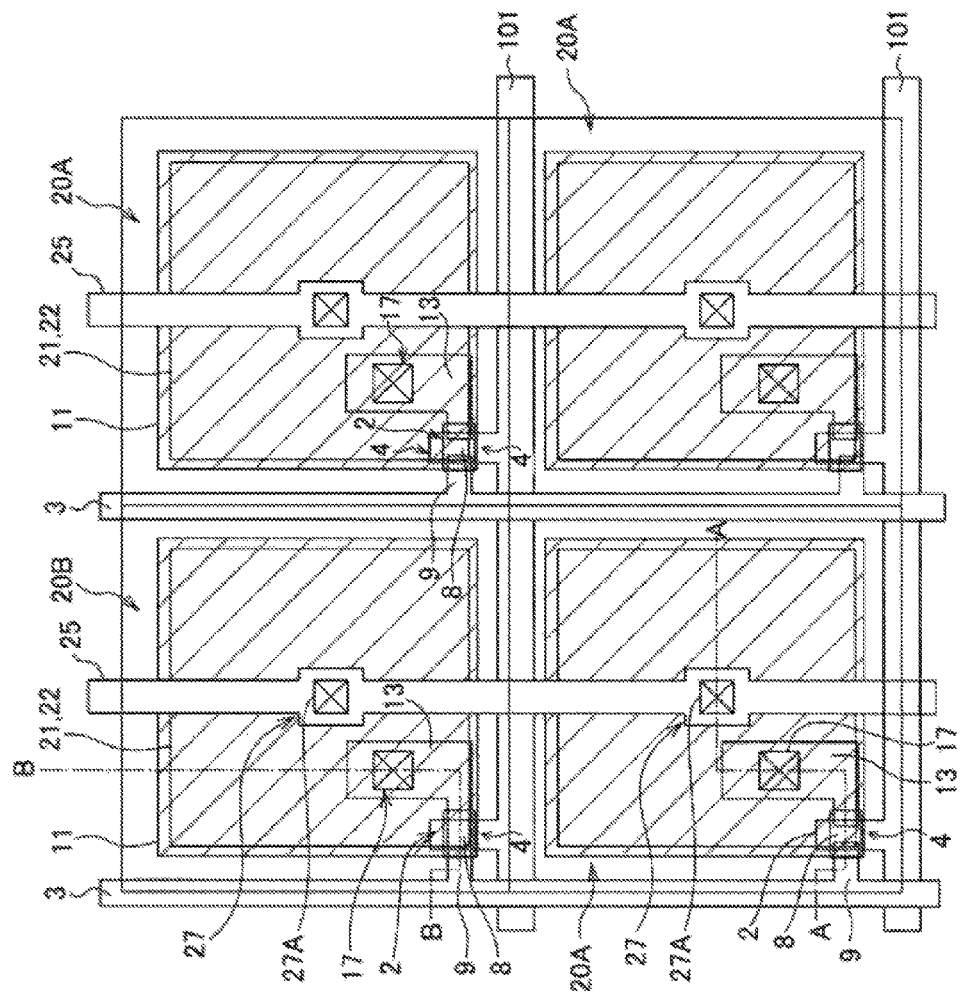
FIG. 4 is a plan diagram showing an example of structure of a radiation detector in accordance with the first exemplary embodiment.

In the radiation detector 10, plural scan lines 101 and plural signal lines 3 are provided mutually orthogonally on a substrate 1 (see FIG. 4). The scan lines 101 are for turning the TFT switches 4 on and off. The signal lines 3 are for reading out the charges accumulated in the sensor portions 103. In the present exemplary embodiment, one of the signal lines 3 is provided at each pixel line in the one direction and one of the scan lines 101 is provided at each pixel line in the intersecting direction. For example, if the pixels 20 are arranged in 1,024 rows by 1,024 columns, 1,024 each of the signal lines 3 and the scan lines 101 are provided.

In the radiographic detector 10, bias lines 25 are provided in parallel with the signal lines 3. One ends and other ends of the bias lines 25 are connected in parallel. The one ends are connected to a power supply 110 that supplies a predetermined bias voltage. The sensor portions 103 are connected to the bias lines 25, and the bias voltage is applied to the sensor portions 103 via the bias lines 25.

Driving signals for switching the TFT switches 4 flow through the scan lines 101. The TFT switches 4 are switched by these driving signals flowing in the scan lines 101.

Electronic signals according to the charges accumulated in the pixels 20 flow into the signal lines 3 when switching states of the TFT switches 4 of the pixels 20 are on. More specifically, if the TFT switch 4 of one of the pixels 20 connected to one of the signal lines 3 is turned on, an electronic signal according to an accumulated charge amount flows into that signal line 3.

A signal detection circuit 105 is connected to the signal lines 3. The signal detection circuit 105 detects electronic signals flowing out through the signal lines 3. A scan line driving circuit 104 is connected to the scan lines 101. The scan line driving circuit 104 outputs driving signals for turning the TFT switches 4 on and off to the scan lines 101. FIG. 2 is simplified to show a single signal detection circuit 105 and scan line driving circuit 104. However, for example, the signal detection circuit 105 and the scan line driving circuit 104 may be plurally provided, and predetermined numbers (for example, 256) of the signal lines 3 and the scan lines 101 are connected to each of the signal detection circuits 105 and scan line driving circuits 104. In this example, if 1,024 each of the signal lines 3 and the scan lines 101 are provided, four of the scan line driving circuits 104 would be provided and sets of 256 of the scan lines 101 connected thereto, and four of the signal detection circuits 105 would be provided and sets of 256 of the signal lines 3 connected thereto.

The signal detection circuit 105 incorporates, for each signal line 3, an amplification circuit 50 that amplifies inputted electronic signals. In the signal detection circuit 105, the electronic signals inputted from the signal lines 3 are amplified by the amplification circuits 50 and outputted to an analog-to-digital (A/D) converter circuit 54.

The amplification circuit 50 is structured as a charge amplification circuit, and is provided with an amplifier 52 such as an operational amplifier or the like, a capacitor C connected in parallel with the amplifier 52, and a charge reset switch SW1 connected in parallel with the amplifier 52.

In the amplification circuit 50, in a state in which the charge reset switch SW1 is in the Off state, charges (electronic signals) are read out from the TFT switch 4 of a pixel 20, the charges read out by the TFT switch 4 are accumulated at the capacitor C, and a voltage value that is outputted from the amplifier 52 in accordance with the accumulated charge amount is amplified.

The control section 106 applies charge reset signals to the charge reset switch SW1 and performs control to turn the charge reset switch SW1 on and off. When the charge reset switch SW1 is turned on, the input side and output side of the amplifier 52 are shorted together and charges at the capacitor C are discharged.

The A/D converter circuit 54 has the function of converting electronic signals that are analog signals inputted from the amplification circuit 50 to digital signals, in a state in which sample-hold (S/H) switches SW of the signal detection circuit 105 are turned on. The A/D converter circuit 54 serially outputs the electronic signals converted to digital signals to the control section 106.

The electronic signals outputted from all the amplification circuits 50 provided in the signal detection circuit 105 are inputted to the A/D converter circuit 54 of the present exemplary embodiment. That is, the signal detection circuit 105 of the present exemplary embodiment is provided with a single A/D converter circuit 54 regardless of the number of amplification circuits 50 (and signal lines 3).

The control section 106 is connected to the signal detection circuit 105 and the scan line driving circuit 104. The control section 106 of the present exemplary embodiment is constituted by a microcomputer, and is provided with a central processing unit (CPU), ROM and RAM, and a non-volatile memory section constituted with flash memory or the like.

The control section 106 executes a program memorized in the ROM with the CPU, and thus performs control for capturing a radiographic image.

The control section 106 of the present exemplary embodiment also has the functions of applying predetermined processing such as noise reduction and the like to the electronic signals detected at the signal detection circuit 105, detecting the start (initiation) of irradiation of radiation and, on the basis of the timing of a detection, outputting control signals indicating signal detection timings to the signal detection circuit 105 and outputting control signals indicating driving signal output timings to the scan line driving circuit 104. The control section 106 of the present exemplary embodiment also includes the function of detecting the start of irradiation of radiation and then, on the basis of the electronic signals read out from the radiation detection pixels 20B, determining whether the electronic signals are caused by noise or are caused by irradiation of the radiation.

The control section 106 applies processing to interpolate image data for the radiation detection pixels 20B (interpolation processing) to the image data to which the above-mentioned predetermined processing has been applied, and generates an image representing the irradiated radiation. That is, the control section 106 generates a radiographic image represented by the irradiated radiation by interpolating image data for the radiation detection pixels 20B on the basis of the image data to which the above-mentioned predetermined processing has been applied.

The radiographic image detector 100 of the present exemplary embodiment is equipped with a reporting section 108. In a case in which the control section 106 determines that the electronic signals are electronic signals caused by noise, the reporting section 108 has the function of reporting this to a user who is capturing the radiographic image. A constitution of the reporting section 108 is not particularly limited, but examples include light-emitting diodes (LEDs) for a visual display, a speaker for an audible report, and the like.

Figure 3A:
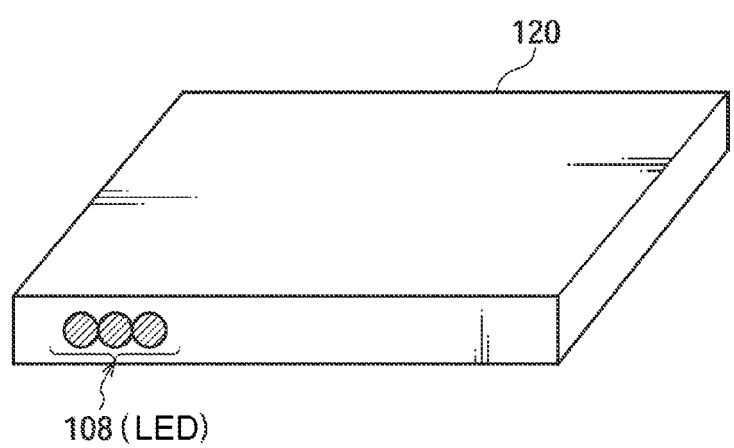
FIG. 3A is a descriptive diagram for describing the external appearance of a radiation detector in accordance with the first exemplary equipment.
Figure 3B:
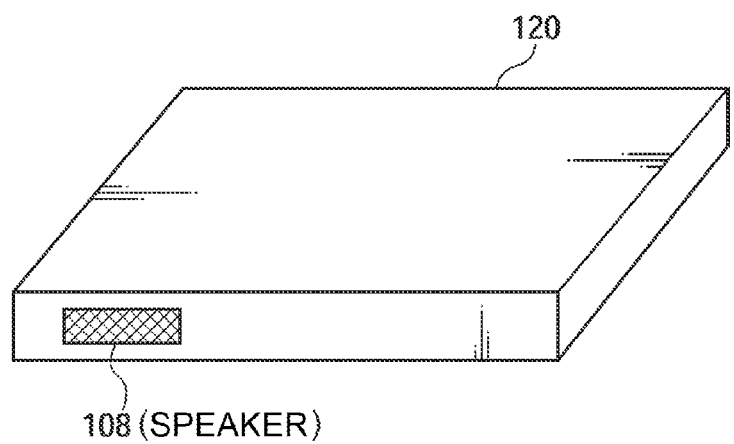
FIG. 3B is a descriptive diagram for describing the external appearance of a radiation detector in accordance with the first exemplary equipment.

In the radiographic image detector 100 of the present exemplary embodiment, the above-mentioned radiation detector 10, A/D converter circuit 54, scan line driving circuit 104, control section 106, signal detection circuit 105 and power supply 110 and the like are accommodated in a casing 120. FIG. 3A and FIG. 3B show the external appearance of the casing 120. FIG. 3A shows a specific example of a case in which the reporting section 108 is LEDs, and FIG. 3B shows a specific example of a case in which the reporting section 108 is a speaker. The reporting section 108 is at a position of the casing 120 that is not irradiated by the radiation (for example, a side face or the like), and is disposed at a position that is easily discerned by users.

Figure 5:
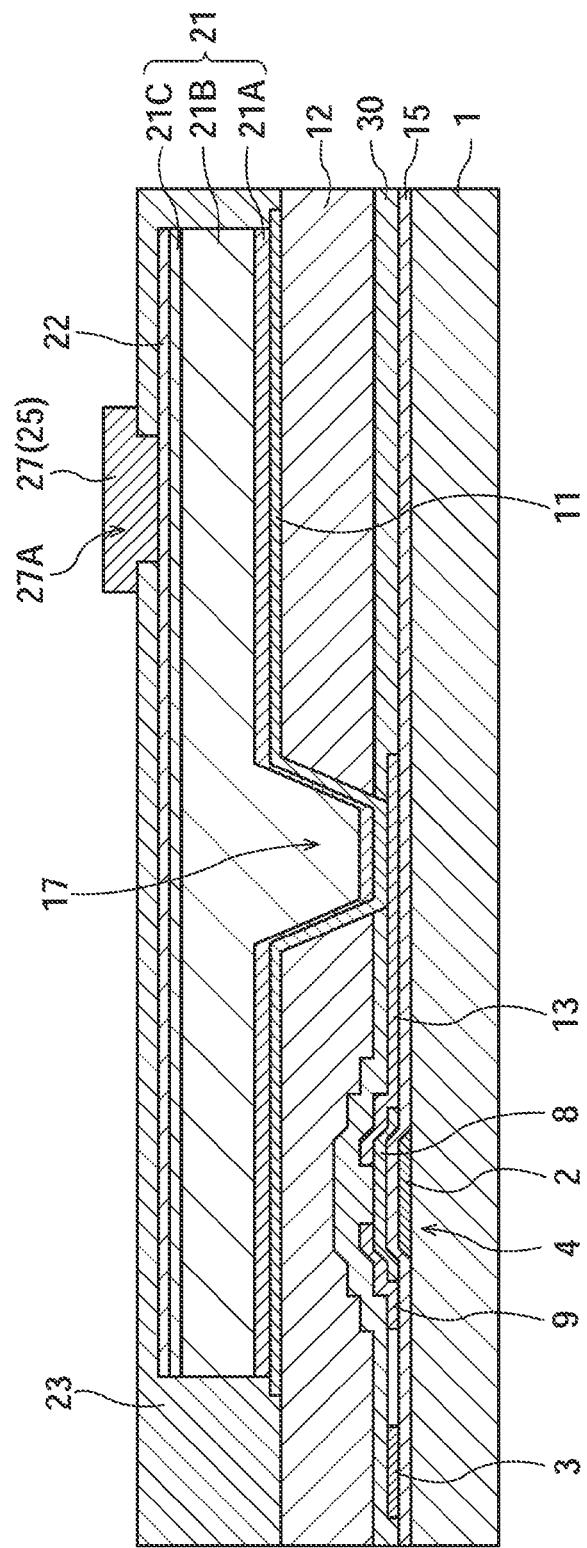
FIG. 5 is a linear sectional diagram of an example of the radiation detector in accordance with the first exemplary embodiment.
Figure 6:
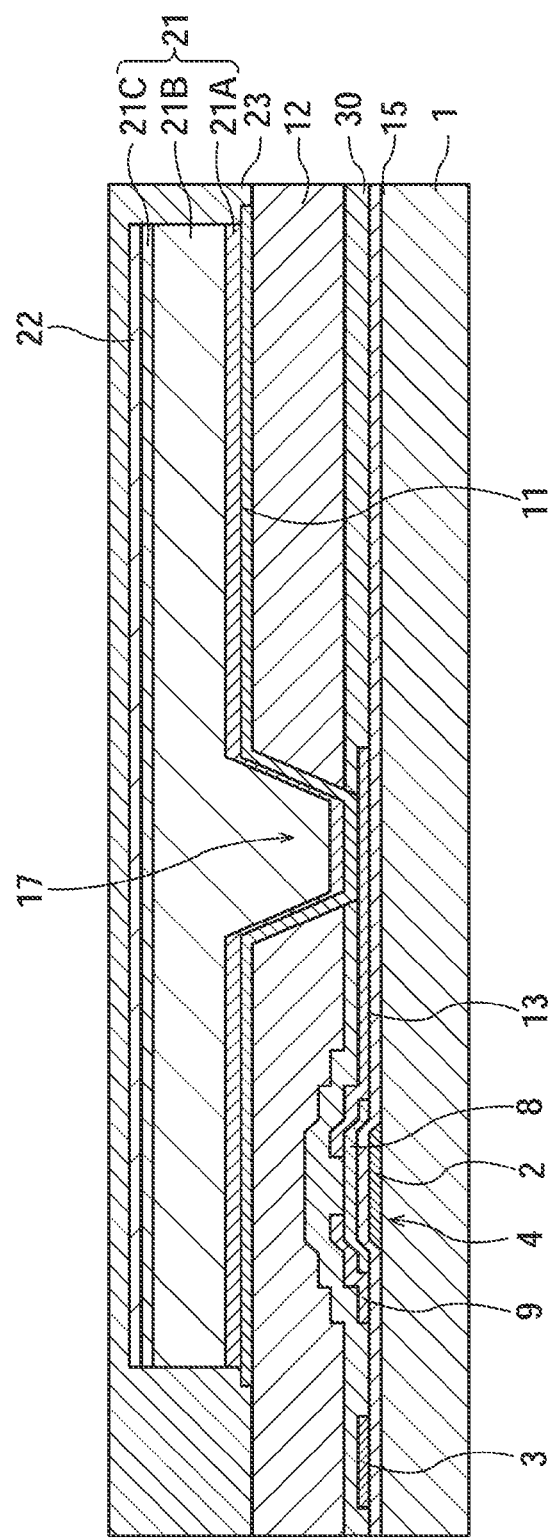
FIG. 6 is a linear sectional diagram of an example of the radiation detector in accordance with the first exemplary embodiment.

FIG. 4 shows a plan diagram illustrating the architecture of the indirect conversion-type radiation detector 10 according to the present exemplary embodiment. FIG. 5 shows a linear sectional diagram of one of the radiation image capturing pixels 20A taken along the line A-A of FIG. 4. FIG. 6 shows a linear sectional diagram of one of the radiation detection pixels 20B taken along the line B-B of FIG. 4.

As shown in FIG. 5, in the pixels 20A of the radiation detector 10, the scan lines 101 (see FIG. 4) and gate electrodes 2 are formed on the insulating substrate 1, which is formed of alkaline-free glass or the like, and the scan lines 101 and gate electrodes 2 are connected (see FIG. 4). A wiring layer in which the scan lines 101 and gate electrodes 2 are formed (this wiring layer is hereinafter referred to as a first signal wiring layer) is formed using aluminium (Al), copper (Cu) or a layered film whose principal constituent is aluminium or copper, but is not limited to these.

An insulating layer 15 is formed over the whole surface of the first signal wiring layer. Portions of the insulating layer 15 that are disposed above the gate electrodes 2 act as gate insulation films of the TFT switches 4. The insulating layer 15 is formed of, for example, SiNx or the like, and is formed by, for example, chemical vapor deposition (CVD) film formation.

A semiconductor active layer 8 is formed on the insulating layer 15 as islands over the gate electrodes 2. The semiconductor active layer 8 is the channel of each TFT switch 4 and is formed of, for example, an amorphous silicon film.

Source electrodes 9 and drain electrodes 13 are formed in a layer thereabove. The signal lines 3 are formed together with the source electrodes 9 and the drain electrodes 13 in the wiring layer in which the source electrodes 9 and the drain electrodes 13 are formed. The source electrodes 9 are connected to the signal lines 3 (see FIG. 4). The wiring layer in which the source electrodes 9, drain electrodes 13 and signal lines 3 are formed (this wiring layer is hereinafter referred to as a second signal wiring layer) is formed using aluminium, copper or a layered film whose principal constituent is aluminium or copper, but is not limited to these. An impurity-doped semiconductor layer (not shown in the drawings), formed of amorphous silicon doped with impurities or the like, is formed between the source electrodes 9 and drain electrodes 13 and the semiconductor active layer 8. The TFT switches 4 for switching are structured by these parts. In the TFT switches 4, the polarity of charges that are collected and accumulated by lower electrodes 11, which are described below, is opposite to the polarity of the source electrodes 9 and the drain electrodes 13.

A TFT protection film layer 30 is formed over substantially the whole area of a region in which the pixels 20 are provided on the substrate 1 (almost the whole region), covering the second signal wiring layer. The TFT protection film layer 30 is for protecting the TFT switches 4 and the signal lines 3 and the like. The TFT protection film layer 30 is formed of, for example, SiNx or the like, and is formed by, for example, CVD film formation.

An interlayer insulating film 12 is formed as a coat on the TFT protection film layer 30. This interlayer insulating film 12 is formed with a film thickness of 1 to 4 μm of a photosensitive organic material with low permittivity (relative permittivity $\epsilon r=2$ to 4) (for example, a positive-type photosensitive acrylic resin such as a material in which a naphthoquinone diazide-based positive-type photosensitivizer is mixed into a base polymer formed of a copolymer of methacrylic acid and glycidyl methacrylate, or the like).

In the radiation detector 10 according to the present exemplary embodiment, a capacitance between metals disposed in a layer above and the layer below the interlayer insulation film 12 is kept low by the interlayer insulation film 12. In addition, this kind of material generally functions as a flattening film, and has an effect of flattening steps of the layers below. In the radiation detector 10 according to the present exemplary embodiment, contact holes 17 are formed at positions of the interlayer insulating film 12 and the TFT protection film layer 30 that oppose the drain electrodes 13.

The lower electrodes 11 of the sensor portions 103 are formed on the interlayer insulating film 12 so as to cover the pixel region and fill in the contact holes 17, and the lower electrodes 11 are connected with the drain electrodes 13 of the TFT switches 4. If semiconductor layers 21, which are described below, have a thickness of around 1 μm, the material of the lower electrodes 11 is hardly at all limited, provided the lower electrodes 11 are conductive. Therefore, there is no problem provided the lower electrodes 11 are formed using a conductive metal such as an aluminium-based material, ITO or the like.

If the film thickness of the semiconductor layers 21 is small (around 0.2-0.5 μm), light is insufficiently absorbed by the semiconductor layers 21. Therefore, in order to prevent an increase in leakage currents caused by illumination of light onto the TFT switches 4, it is preferable if the semiconductor layers 21 are alloys or a layered film with a light-blocking metal as a principal constituent.

The semiconductor layers 21, which function as photodiodes, are formed on the lower electrodes 11. In the present exemplary embodiment, PIN-architecture photodiodes, in which an n+ layer, an i layer and a p+ layer are layered (n+amorphous silicon, amorphous silicon, and p+amorphous silicon), are employed as the semiconductor layers 21. The semiconductor layers 21 are formed by an n+ layer 21A, an i layer 21B and a p+ layer 21C being layered in this order from the lowest layer. The i layer 21B generates charges (pairs of free electrons and free holes) when illuminated with light. The n+ layer 21A and the p+ layer 21C function as contact layers and electrically connect the lower electrodes 11 and upper electrodes 22, which are described below, with the i layer 21B.

The upper electrodes 22 are respectively individually formed on the semiconductor layers 21. A material with high light transmissivity such as, for example, ITO, IZO (indium zinc oxide) or the like is used for the upper electrodes 22. In the radiographic detector 10 according to the present exemplary embodiment, the sensor portions 103 include the upper electrodes 22, the semiconductor layers 21 and the lower electrodes 11.

A coat-form interlayer insulating film 23 is formed over the interlayer insulating film 12, the semiconductor layers 21 and the upper electrodes 22, so as to cover the semiconductor layers 21 but with openings 27A at portions that correspond with the upper electrodes 22.

The bias lines 25 are formed over the interlayer insulating film 23, of aluminium, copper, or an alloy or layered film with aluminium or copper as a principal constituent. Contact pads 27 are formed on the bias lines 25 near the openings 27A. The contact pads 27 are electrically connected with the upper electrodes 22 through the openings 27A in the interlayer insulating film 23.

In contrast, at each radiation detection pixel 20B of the radiation detector 10, as shown in FIG. 6, the TFT switch 4 is formed such that the source electrode 9 and the drain electrode 13 are in contact. That is, in the pixel 20B, the source and drain of the TFT switch 4 are short-circuited. Therefore, charges collected at the lower electrode 11 of the pixel 20B flow into the signal line 3 regardless of the switching state of the TFT switch 4.

A scintillator is provided on the surface of the radiation detector 10 that is formed in this manner. For example, if required, a protective film is formed of an insulating material with low light absorption and the scintillator, formed of GOS or the like, is pasted onto the surface of the radiation detector 10 using an adhesive resin with low light absorption. As a further example, a scintillator formed of CsI or the like is directly vapor-deposited onto the surface of the radiation detector 10. CsI may be vapor-deposited onto a support and then pasted onto the surface of the radiation detector 10 using an adhesive resin with low light absorption.

Figure 7A:
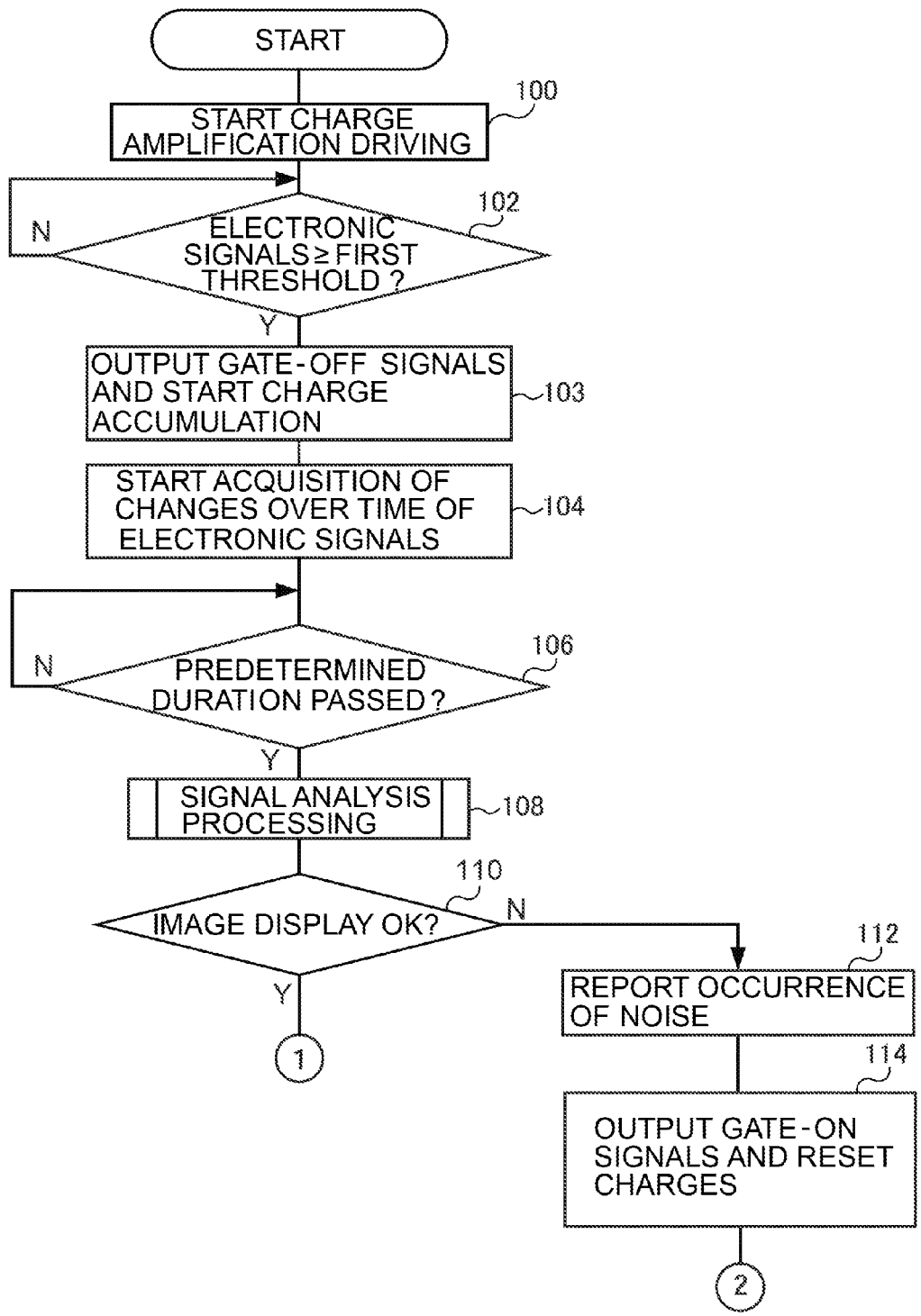

Next, a flow of operations when a radiographic image is being captured by the radiographic image detector 100 with the above-described structure is described. In the present exemplary embodiment, a radiographic image is captured under the control of the control section 106 in accordance with instructions from the control device 202. At the control section 106, when an image capture instruction is received from the control device 202, the following processing is executed by a radiation image capture program being executed by the CPU. A flowchart of an example of overall flow of this processing is shown in FIGS. 7A and 7B. The radiation image capture program may be memorized in the radiographic image detector 100 in advance, and may be provided from a CD-ROM, through a USB, or from outside the control device 202 and the like.

When the image capture instruction is received from the control device 202, in step 100, the control section 106 starts driving of the amplifiers 52 of the amplification circuits 50 of the signal detection circuit 105, and drives the same continuously. Thus, the control section 106 acquires electronic signals outputted from the radiation detection pixels 20B to the signal lines 3 (i.e., values thereof converted to digital signals, which are hereinafter referred to simply as electronic signals).

Then, in step 102, the control section 106 compares the acquired electronic signals with a pre-specified first threshold for detecting the start of irradiation of the radiation, and detects whether or not irradiation of the radiation has started from whether or not the acquired electronic signals are at or above the first threshold. Detection of the start of irradiation of the radiation by the control section 106 is not limited to whether or not the first threshold for radiation detection is exceeded. For example, the start of irradiation may be detected on the basis of pre-specified conditions such as a number of times the first threshold is exceeded and the like. If the electronic signals are below the first threshold, the result of the determination is negative—an irradiation of the radiation has not started—and the control section 106 goes into a standby state. On the other hand, if the electronic signals are at least at the first threshold, the result of the determination is affirmative—an irradiation of the radiation has started—and the control section 106 proceeds to step 103.

In step 103, in order to start the capture of the radiographic image, the control section 106 instructs the scan line driving circuit 104 to output driving signals that are gate-off signals (signals to put the gates of the TFT switches 4 into Off states). Hence, at the sensor portions 103 of the radiation image capturing pixels 20A, the accumulation of charges generated in accordance with the irradiation of radiation is begun. However, at the radiation detection pixels 20B, charges generated in accordance with the irradiation of radiation are outputted to the signal lines 3 regardless of the gate-off signals.

In step 104, the control section 106 starts to acquire changes over time of the driving signals outputted from the radiation detection pixels 20B to the signal lines 3. Then, in step 106, a determination is made as to whether a pre-specified predetermined duration for acquiring the changes over time has passed. If the predetermined duration has not passed, the acquisition of changes over time of the electronic signals continues. However, if the predetermined duration has passed, the acquisition of changes over time of the electronic signals stops and the control section 106 proceeds to step 108. This predetermined duration is a duration suitable for detecting noise, which is specified in advance from prior testing or the like.

In step 108, the presence or absence, a strength and a duration of noise are detected by signal analysis processing.

Figure 8:
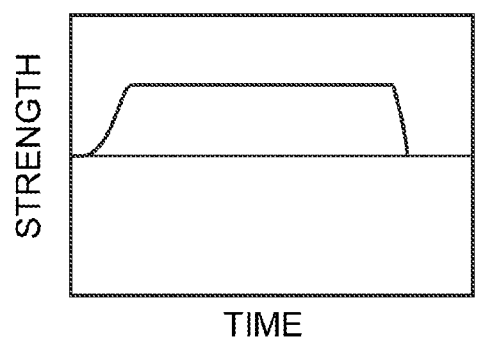
FIG. 8 is a descriptive diagram for describing electronic signals according to irradiated radiation.
Figure 9A:
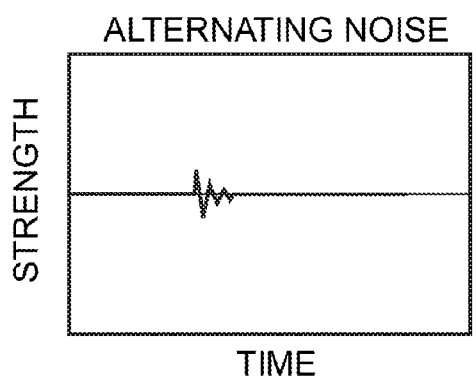
FIG. 9A is a descriptive diagram for describing noise, illustrating alternating noise.
Figure 9B:
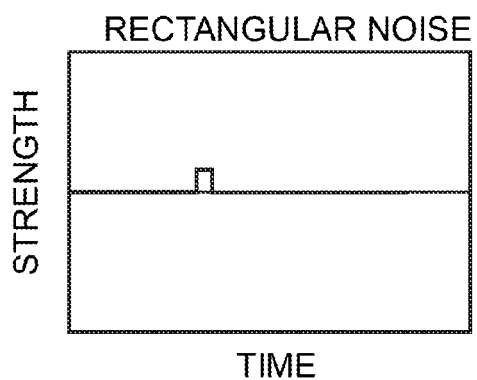
FIG. 9B is a descriptive diagram for describing noise, illustrating rectangular noise.

Now, before a description of the signal analysis processing of the present exemplary embodiment, noise that occurs in the radiation image capturing device 201 (the radiographic image detector 100) is described. FIG. 8 shows a specific example of changes over time in the strength of irradiated radiation (and electronic signals produced by the radiation). Noise that appears in the electronic signals is broadly divided into two kinds of noise. Alternating noise in which the waveform of electronic signals caused by the noise is an alternating wave (see FIG. 9A); and rectangular noise in which the waveform of the electronic signals caused by the noise is a rectangular wave (see FIG. 9B). Alternating noise includes noise produced from other electronic devices and the like, and impact noise produced by an impact being applied to the signal lines 3, cable wiring of the radiation detector 10 or the like. FIG. 9A shows alternating noise with a low strength and a short duration of occurrence. Meanwhile, rectangular noise includes pressure on the sensor portions 103 of the radiographic image detector 100 (charge generation due to piezoelectric effects), and rectangular noise produced by an increase in dark current due to effects such as a rise in temperature of the sensor portions 103 and the like. FIG. 9B shows rectangular noise with a low strength and a short duration of occurrence.

Below, as a specific example, details of a case in which the occurring noise is alternating noise are described. Obviously, a case with rectangular noise is similar.

Figure 10:
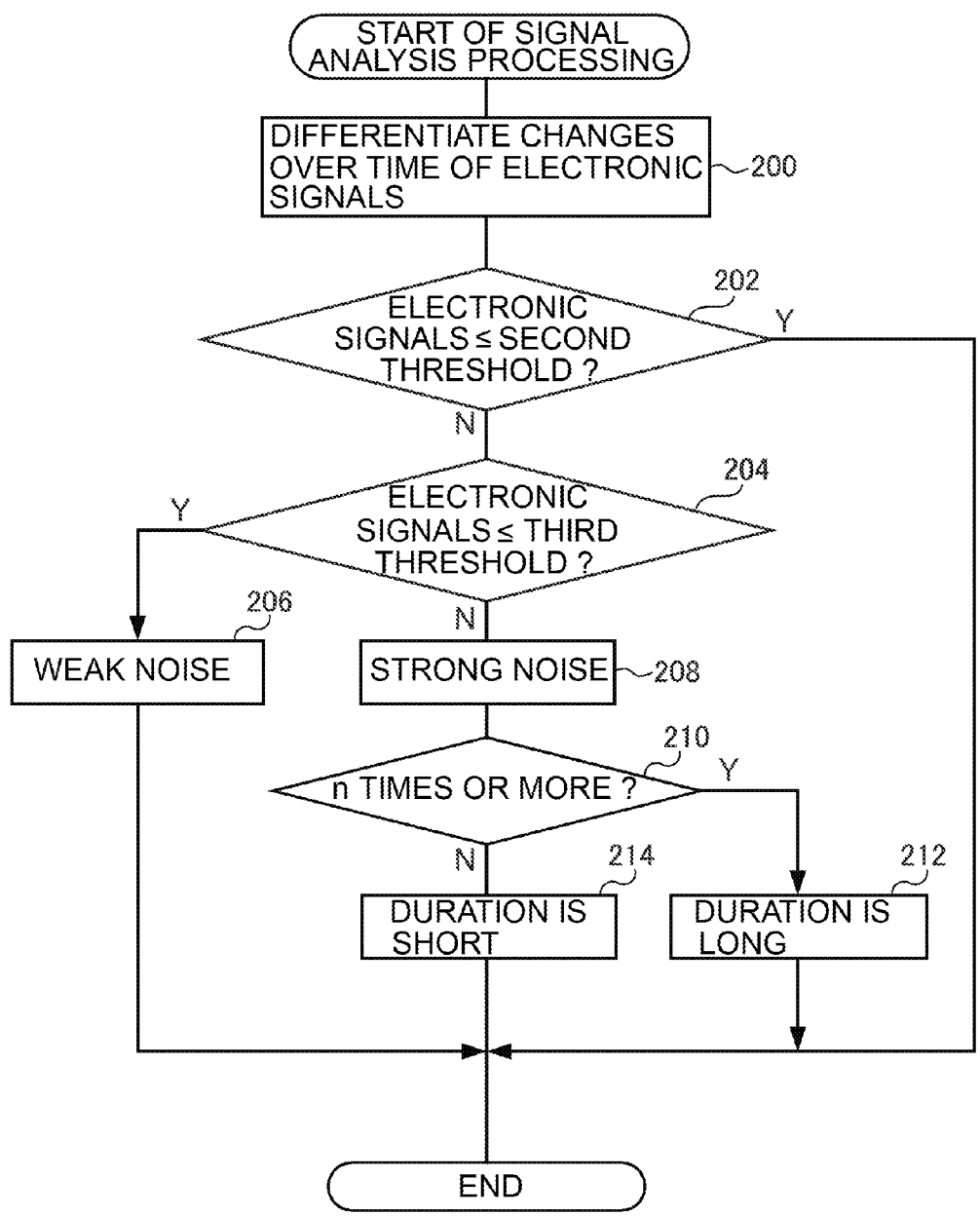
FIG. 10 is a flowchart of an example of signal analysis processing in the radiation image capturing device in accordance with the first exemplary embodiment.

FIG. 10 shows a flowchart of a specific example of flow of the signal analysis processing of the present exemplary embodiment.

Figure 11A:
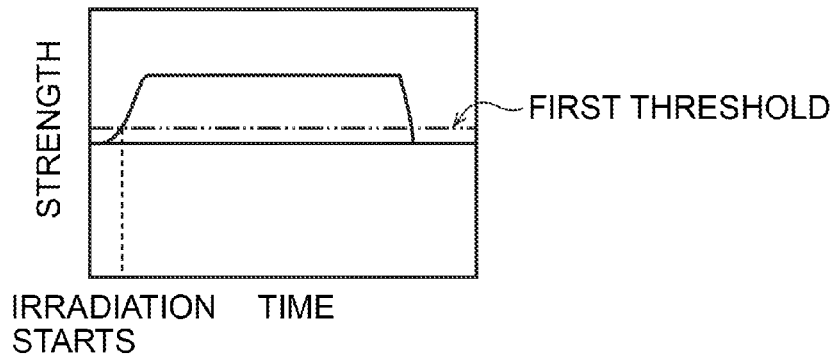
FIG. 11A is a descriptive diagram for describing a profile of changes over time of strength before differentiation processing is carried out in the first exemplary equipment, illustrating a case in which noise is not included.
Figure 11B:
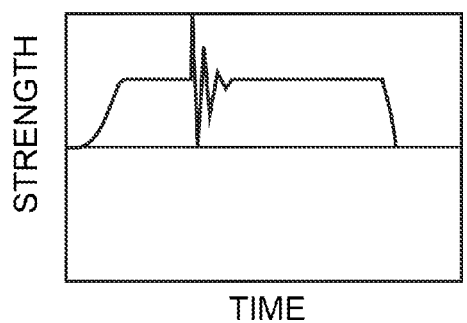
FIG. 11B is a descriptive diagram for describing a profile of changes over time of strength before the differentiation processing is carried out in the first exemplary equipment, illustrating a case in which alternating noise with a high strength and a short duration occurs.
Figure 11C:
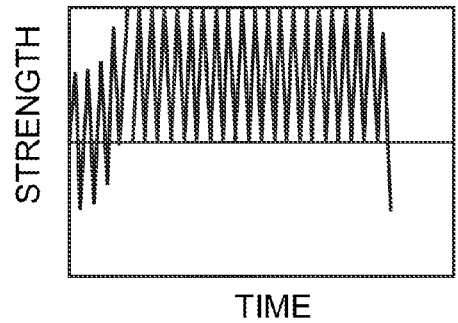
FIG. 11C is a descriptive diagram for describing a profile of changes over time of strength before the differentiation processing is carried out in the first exemplary equipment, illustrating a case in which alternating noise with a high strength and a long duration occurs.

In step 200, differentiation processing is applied to the changes over time of the electronic signals. As the differentiation processing, ordinary differentiation processing may be applied. As specific examples, FIG. 11A to FIG. 11C show profiles of changes over time of the strength of the electronic signals before being differentiated. FIG. 11A shows changes over time of the strength of electronic signals based only on charges generated by an irradiation of radiation, in which noise is not present. FIG. 11B shows a case in which, if alternating noise with a high strength and a short duration is produced, the electronic signals caused by this alternating noise are added to the electronic signals shown in FIG. 11A. FIG. 11C shows a case in which, if alternating noise with a high strength and a long duration is produced, the electronic signals caused by this alternating noise are added to the electronic signals shown in FIG. 11A.

Figure 12A:
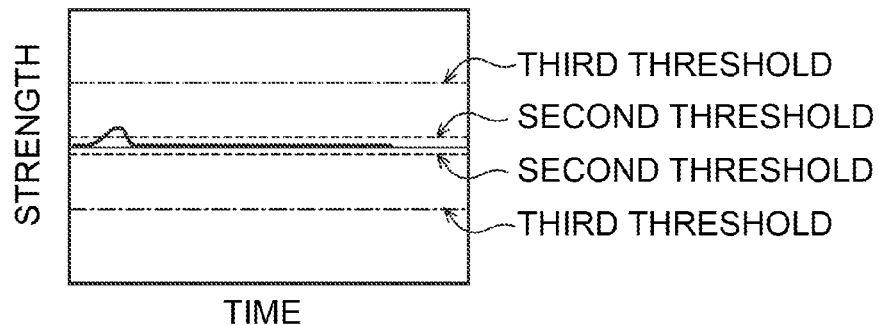
FIG. 12A is a descriptive diagram for describing a profile of changes over time of strength after the differentiation processing is carried out in the first exemplary equipment, illustrating the case in which noise is not included.
Figure 12B:
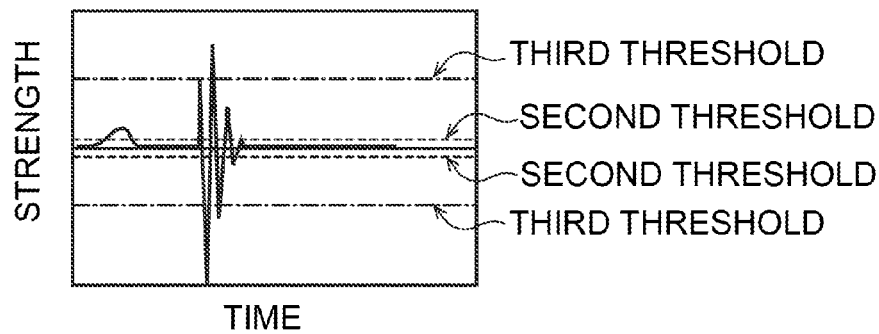
FIG. 12B is a descriptive diagram for describing a profile of changes over time of strength after the differentiation processing is carried out in the first exemplary equipment, illustrating the case in which alternating noise with a high strength and a short duration occurs.
Figure 12C:
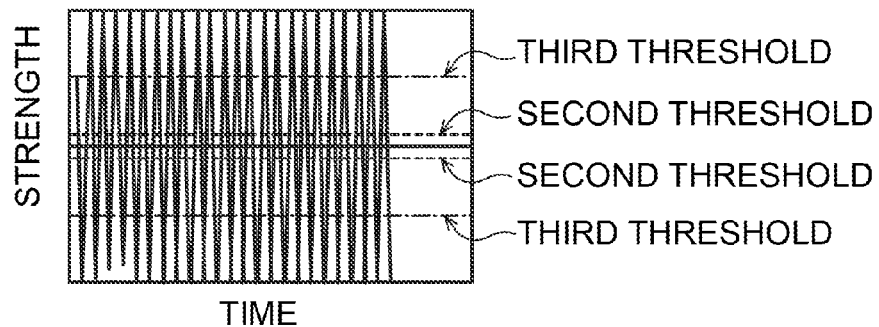
FIG. 12C is a descriptive diagram for describing a profile of changes over time of strength after the differentiation processing is carried out in the first exemplary equipment, illustrating the case in which alternating noise with a high strength and a long duration occurs.

Also as specific examples, FIG. 12A to FIG. 12C show profiles of changes over time of the strength of electronic signals to which the changes over time of the electronic signals shown in FIG. 11A to FIG. 11C are differentiated. FIG. 12A corresponds to FIG. 11A, FIG. 12B corresponds to FIG. 11B, and FIG. 12C corresponds to FIG. 11C.

In the present exemplary embodiment, a second threshold for detecting the presence of noise and a third threshold for detecting the strength of noise are specified in advance. In step 202, a determination is made as to whether or not the strengths of the differentiated electronic signals (hereinafter, where there is no need to distinguish these from the signals before differentiation processing, these are simply referred to as electronic signals) are less than or equal to the second threshold. Then, in step 204, a determination is made as to whether or not the strengths of the electronic signals are less than or equal to the third threshold. Both positive and negative values are specified for the second threshold and the third threshold, and it is determined that the second threshold or third threshold has been exceeded if the strengths of the differentiated electronic signals reach both the positive and negative values. In the present exemplary embodiment, the second threshold is less than the third threshold.

FIG. 13 shows a specific example of determinations of noise in the signal analysis of the present exemplary embodiment. In the present exemplary embodiment, if the strength of the electronic signals is at or below the second threshold, no occurrence of noise is detected, whereas if the strength of the electronic signals exceeds the second threshold, an occurrence of noise is detected. In a case in which an occurrence of noise is detected (the strength of the electronic signals exceeds the second threshold), then if the strength of the electronic signals is at or below the third threshold, it is detected that the strength of the occurring noise is low. However, if the strength of the electronic signals exceeds the third threshold, it is detected that the strength of the occurring noise is high.

In the signal analysis of the present exemplary embodiment, the duration of the noise is detected on the basis of a number of times the strength of the electronic signals exceeds the third threshold in a pre-specified unit of time. In the present exemplary embodiment, if the number of times the strength of the electronic signals exceeds the third threshold is less than a number n, then it is detected that the duration of the noise is short, whereas if the number of times the strength of the electronic signals exceeds the third threshold is equal to or greater than n, then it is detected that the duration of the noise is long. The above-mentioned unit of time and number n may be found in advance by testing and the like. In the present exemplary embodiment, the detection of the length of a duration of noise is not limited to the number of times the third threshold is exceeded. For example, the duration may be detected from a number of times the second threshold is exceeded.

In the above-described step 202, if the electronic signals are equal to or below the second threshold, no occurrence of noise is detected. Therefore, the result of the determination is affirmative and the present processing ends. However, if the electronic signals are above the second threshold, an occurrence of noise is detected, so the result of the determination is negative, and the control section 106 proceeds to step 204. In step 204, if the electronic signals are equal to or below the third threshold, the result of the determination is affirmative, then the processing proceeds to step 206, It is detected that the noise is weak noise, and then the signal analysis processing ends. On the other hand, if the electronic signals exceed the third threshold, the result of the determination is negative, then the control section 106 proceeds to step 208. It is detected that the noise is strong noise, and then the control section 106 proceeds to step 210.

In step 210, a determination is made as to whether or not the number of times the electronic signals are at or above the third threshold is at least the above-mentioned number n. If the number of times is at least n, the result of the determination is affirmative, and the control section 106 proceeds to step 212. It is detected that the duration of the noise is long, and the signal analysis processing ends. On the other hand, if the number of times is less than n, the result of the determination is negative and the control section 106 proceeds to step 214. It is detected that the duration of the noise is short, and the signal analysis processing ends.

Hence, when the signal analysis processing (step 108 in FIG. 7) ends, the control section 106 of the radiographic image detector 100 proceeds to step 110. In step 110, on the basis of the results of the signal analysis processing, a determination is made as to whether or not to display the radiographic image. In the present exemplary embodiment, the captured radiographic image is outputted from the control section 106 to the control device 202 and displayed at the display section 212 of the control device 202. Correspondingly, in the present exemplary embodiment, if it is determined that the radiographic image should not be displayed, the radiographic image is not outputted from the control section 106 to the control device 202.

In the present exemplary embodiment, if an occurrence of noise is detected and it is detected that the strength of the occurring noise is high and the duration is long, display of the radiographic image is prevented. Accordingly, if it is detected by the signal analysis processing that the strength of the occurring noise is high and the duration is long, the result of the determination in step 110 is negative and the control section 106 proceeds to step 112. In step 112, the user capturing the radiographic image is notified by the reporting section 108 that noise with a high strength and a long duration has occurred. As a specific example, if the reporting section 108 is constituted by LEDs in the present exemplary embodiment (see FIG. 3A), the LEDs are flashed at 0.2-second intervals to report to the user and thus give a strong warning. If the reporting section 108 is constituted by LEDs and a speaker, the LEDs may be flashed at 0.1-second intervals and a sound generated by the speaker to report to the user and thus give a strong warning. Methods of reporting are not limited thus, and are not particularly limited, provided cases of weak noise and short-duration noise, which are described below, may be distinguished. The display section 212 and reporting section 213 or the like of the control device 202 may be used instead of the reporting section 108 of the radiographic image detector 100, or both the radiographic image detector 100 and the control device 202 may be used. In the present exemplary embodiment, the radiographic image is not displayed (outputted) if there is high-strength, long-duration noise. Accordingly, an indication thereof may be displayed at the display section 212 of the control device 202, and an indication prompting the user to repeat the image capture may be displayed.

By being notified as described above, the user may recognize the occurrence of high-strength, long-duration noise. Accordingly, the user may stop the capture of the radiographic image and repeat the image capture as appropriate. As a specific example, the imaging subject 206 may be taken out of position and a noise source identified and removed. Then the imaging subject 206 is positioned again and the control device 202 is instructed to capture a radiographic image. Furthermore, because the user may recognize an occurrence of noise from the reporting described above, the user may repeat image capture without being disconcerted by the lack of display of a radiographic image.

In a case in which high-strength, long-duration noise occurs, the radiation irradiation device 204 may be instructed to stop the irradiation of radiation, via the control device 202. Thus, an amount of exposure of the imaging subject 206 may be reduced.

After the user has been notified, in step 114, the control section 106 instructs that driving signals that are gate-on signals (signals putting the gates of the TFT switches 4 into the On state) should be outputted, and the charges accumulated at the sensor portions 103 of the radiation image capturing pixels 20A are reset. Thereafter, the present processing ends. In the present exemplary embodiment, because the radiographic image is not generated in this case, the charges accumulated in the radiation image capturing pixels 20A are reset to prepare for repeating image capture. At this time, because the gate-on signals are being outputted in order to reset the charges accumulated in the radiation image capturing pixels 20A, the on signals may be outputted to all the radiation image capturing pixels 20A (the scan lines 101) simultaneously. After the charges accumulated at the sensor portions 103 of the radiation image capturing pixels 20A have been reset, the control section 106 returns to the state in step 100 in which the amplifiers 52 are continuously driven.

Alternatively, if no noise occurs, or if noise occurs that has one or both of a low strength and a short duration, the radiographic image should be displayed (captured). Accordingly, the result of the determination in step 110 is affirmative and the control section 106 proceeds to step 116. In step 116, a determination is made as to whether noise has occurred. If noise has not occurred, the result of the determination is negative and the control section 106 proceeds to step 120. However, if one or both of low-strength noise and short-duration noise has occurred, the result of the determination is affirmative, the control section 106 proceeds to step 118, and the user capturing the radiographic image is notified by the reporting section 108 that one or both of low-strength noise and short-duration noise has occurred. As a specific example, if the reporting section 108 is constituted by LEDs in the present exemplary embodiment (see FIG. 3A), the LEDs are flashed at 0.5-second intervals to report to the user and thus give a strong warning. If the reporting section 108 is constituted by LEDs and a speaker, a warning sound may be generated by the speaker at 0.5-second intervals to report to the user and thus give a strong warning. Methods of reporting are not limited thus, and are not particularly limited, provided the above-mentioned case of high-strength, long-duration noise may be distinguished from. Similarly to the above-mentioned case, the display section 212 and reporting section 213 or the like of the control device 202 may be used instead of the reporting section 108 of the radiographic image detector 100, or both the radiographic image detector 100 and the control device 202 may be used.

Thus, by being notified, the user may recognize the occurrence of the one or both of low-strength noise and short-duration noise before the radiographic image is displayed. Therefore, in a case in which the radiographic image is an anomalous image, repeated image capture may be prepared for. As a specific example, with the imaging subject 206 staying in position after the capture of the radiographic image, the imaging subject 206 may be instructed not to move their body, the displayed radiographic image may be checked, and then the image capture may be promptly repeated. The image capture need not be repeated if a level of anomalies appearing in the radiographic image is low when the radiographic image is checked; for example, if image blurring occurs at a height level outside a range of interest or the like.

Then, in step 120, a determination is made as to whether a pre-specified charge accumulation duration for capturing the radiographic image has passed. If the accumulation duration has not passed, the result of the determination is negative, and the control section 106 is in the standby state. On the other hand, if the accumulation duration has passed, the result of the determination is affirmative and the control section 106 proceeds to step 122. In step 122, because it is necessary to acquire electronic signals from each pixel 20 (each of the radiation image capturing pixels 20A), the control section 106 instructs sequential output of driving signals that are gate-on signals (signals putting the gates of the TFT switches 4 into the On state) to each of the scan lines 101, and the electronic signals are acquired in accordance with the charges accumulated at the sensor portions 103 of the radiation image capturing pixels 20A. The control section 106 generates the radiographic image on the basis of the acquired electronic signals. Then, in step 124, the control section 106 outputs the generated radiographic image to the control device 202 so as to be displayed, after which the present processing ends.

As described above, in the radiation image capturing device 201 of the present exemplary embodiment, when the capture of a radiographic image is instructed, electronic signals corresponding to charges outputted from the radiation detection pixels 20B are compared with the first threshold by the control section 106 of the radiographic image detector 100, and if the electronic signals exceed the first threshold, the control section 106 detects that an irradiation of radiation has started. If an irradiation of radiation has started, the control section 106 performs control such that charges are accumulated in the sensor portions 103 of the radiation image capturing pixels 20A, and acquires changes over time of the electronic signals corresponding to charges outputted from the radiation detection pixels 20B. The control section 106 differentiates the changes over time of the acquired electronic signals in the signal analysis, and if the second threshold is exceeded, detects that noise has occurred. Further, if the third threshold is exceeded, the control section 106 detects that the strength of the occurring noise is high, and if a number of times the third threshold is exceeded is equal to or greater than n, the control section 106 detects that the duration of the noise is long. If the strength of the occurring noise is high and the duration is long, this is reported to a user by the reporting section 108, and the radiographic image is not generated and displayed (outputted). Alternatively, if the noise has one or both of a low strength and a short duration, this is reported to the user by the reporting section 108, and the radiographic image is generated and displayed at the display section 212 of the control device 202.

Thus, in the radiation image capturing device 201 of the present exemplary embodiment, the presence or absence of noise when a radiographic image is being captured may be appropriately detected and reported.

As a comparative example, a radiographic image is captured by a radiation image capturing device that does not perform the signal analysis processing of acquired electronic signals that is performed by the above-described control section 106, that is, does not detect the presence or absence of noise, and that is not equipped with the reporting section 108. In this case, unlike the above-described present exemplary embodiment, a user may not recognize that noise has occurred during the capture of a radiographic image until the radiographic image is displayed. Consequently, the user has to position the imaging subject 206 again and repeat the image capture. As a further comparative example, a radiographic image is captured by a radiation image capturing device that does perform the signal analysis processing of acquired electronic signals that is performed by the above-described control section 106 (the detection of the presence or absence of noise) but is not equipped with the reporting section 108. In this case, if noise with a high strength and a long duration occurs, the radiographic image is not displayed, a user may mistakenly think that the radiation image capturing device is malfunctioning, and may repeat the image capture with another radiation image capturing device or the like. Further, if there is one or both of low-strength noise and short-duration noise, the user may not recognize this until the radiographic image in which the noise occurs is displayed. Consequently, the user has to position the imaging subject 206 again and repeat the image capture.

In contrast, with the present exemplary embodiment, the presence or absence of noise when a radiographic image is being captured may be suitably detected and reported as described above. Therefore, the burden on a user may be moderated. Furthermore, in a case in which image capture is to be repeated, the repeat image capture may be performed quickly. Moreover, because it may easily be recognized whether or not there is an anomaly due to noise in a radiographic image, the likelihood of misdiagnosis may be suppressed.

Second Exemplary Embodiment

Next, a second exemplary embodiment is described.

The pixels 20 and radiographic image detector 100 of the present exemplary embodiment have substantially the same structures and operations as in the first exemplary embodiment. Therefore, portions that are the same will not be described. The radiographic image detector 100 according to the present exemplary embodiment differs in a portion of the aforementioned signal analysis processing (see FIG. 10). Therefore, only the processing that is different is described.

Figure 15A:
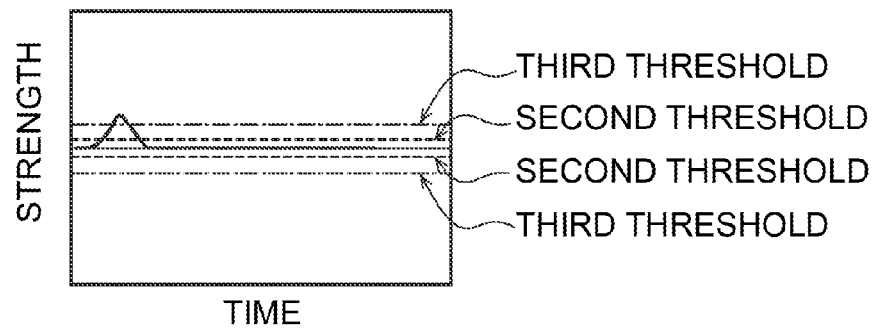
FIG. 15A is a descriptive diagram for describing a profile of changes over time of strength after differentiation processing is carried out in a second exemplary equipment, illustrating a case in which noise is not included.
Figure 15B:
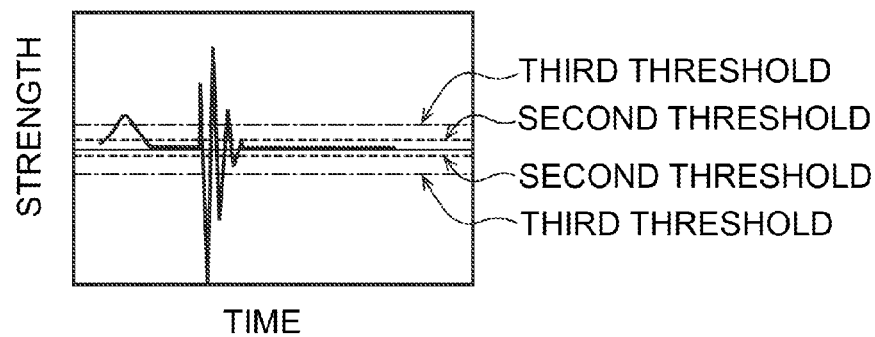
FIG. 15B is a descriptive diagram for describing a profile of changes over time of strength after the differentiation processing is carried out in the second exemplary equipment, illustrating a case in which alternating noise with a high strength and a short duration occurs.
Figure 15C:
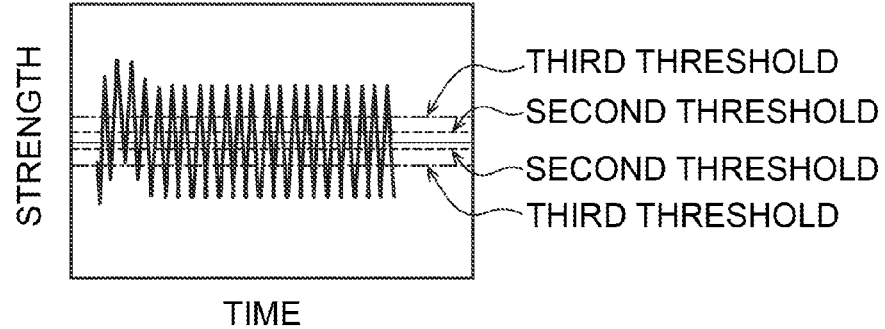
FIG. 15C is a descriptive diagram for describing a profile of changes over time of strength after the differentiation processing is carried out in the second exemplary equipment, illustrating a case in which alternating noise with a high strength and a long duration occurs.

FIG. 14 shows a flowchart of an example of the signal analysis processing according to the present exemplary embodiment. In the present exemplary embodiment, instead of the differentiation processing performed in the first exemplary embodiment, differences from a moving average of the changes over time of the electronic signals are used. Accordingly, in step 300, a moving average of changes over time of the electronic signals is taken. Then, in step 301, the moving average is subtracted from the electronic signal at a current point in time to calculate a difference. As specific examples, FIG. 15A to FIG. 15C show profiles of changes over time in strengths of differences from the moving averages of the changes over time of the electronic signals shown in FIG. 11A to FIG. 11C. FIG. 15A corresponds with FIG. 11A, FIG. 15B corresponds with FIG. 11B and FIG. 15C corresponds with FIG. 11C.

Step 302 corresponds with step 202 of the signal analysis processing of the first exemplary embodiment (see FIG. 10), and compares the differences with a second threshold. Step 304 corresponds with step 302 of the signal analysis processing of the first exemplary embodiment (see FIG. 10), and compares the differences with a third threshold. Thereafter, steps 306 to 314 of the signal analysis processing of the present exemplary embodiment correspond with steps 206 to 214, respectively, of the signal analysis processing of the first exemplary embodiment and carry out the same processing.

Thus, in the present exemplary embodiment, the presence or absence, strength and duration of noise are detected using differences from the moving average of the changes over time of electronic signals. Therefore, similarly to the first exemplary embodiment, in the radiation image capturing device 201 of the present exemplary embodiment, the presence or absence of noise when a radiographic image is being captured may be suitably detected and reported.

Third Exemplary Embodiment

Next, a third exemplary embodiment is described. In the present exemplary embodiment, structures and operations that are substantially the same as in the first exemplary embodiment are not described. In the first exemplary embodiment, the control section 106 combines the electronic signals outputted from the radiation detection pixels 20B to the signal lines 3 and acquires a single electronic signal. In contrast, the radiographic image detector 100 of the present exemplary embodiment is constituted to acquire the electronic signals outputted from each of the signal lines 3 (the amplification circuits 50), detect whether noise is present or absent in the acquired electronic signals, and report the same.

FIG. 16 shows a schematic diagram showing an example of overall structure of the radiographic image detector 100 according to the present exemplary embodiment. In the present exemplary embodiment, an example of the radiographic image detector 100 is illustrated for a case in which the radiation detection pixels 20B are provided at each of the signal lines 3. In order to distinguish the electronic signals outputted from each of the signal lines 3 (D1 to D4), when distinguishing the respectively connected amplification circuits 50 and the like of the signal detection circuit 105, numbers are appended in order to distinguish the individuals, such as amplification circuits $50_1$ to $50_4$ as shown in FIG. 16, and in cases of referring to the same in general, they are simply referred to as the amplification circuits 50.

Figure 17B:
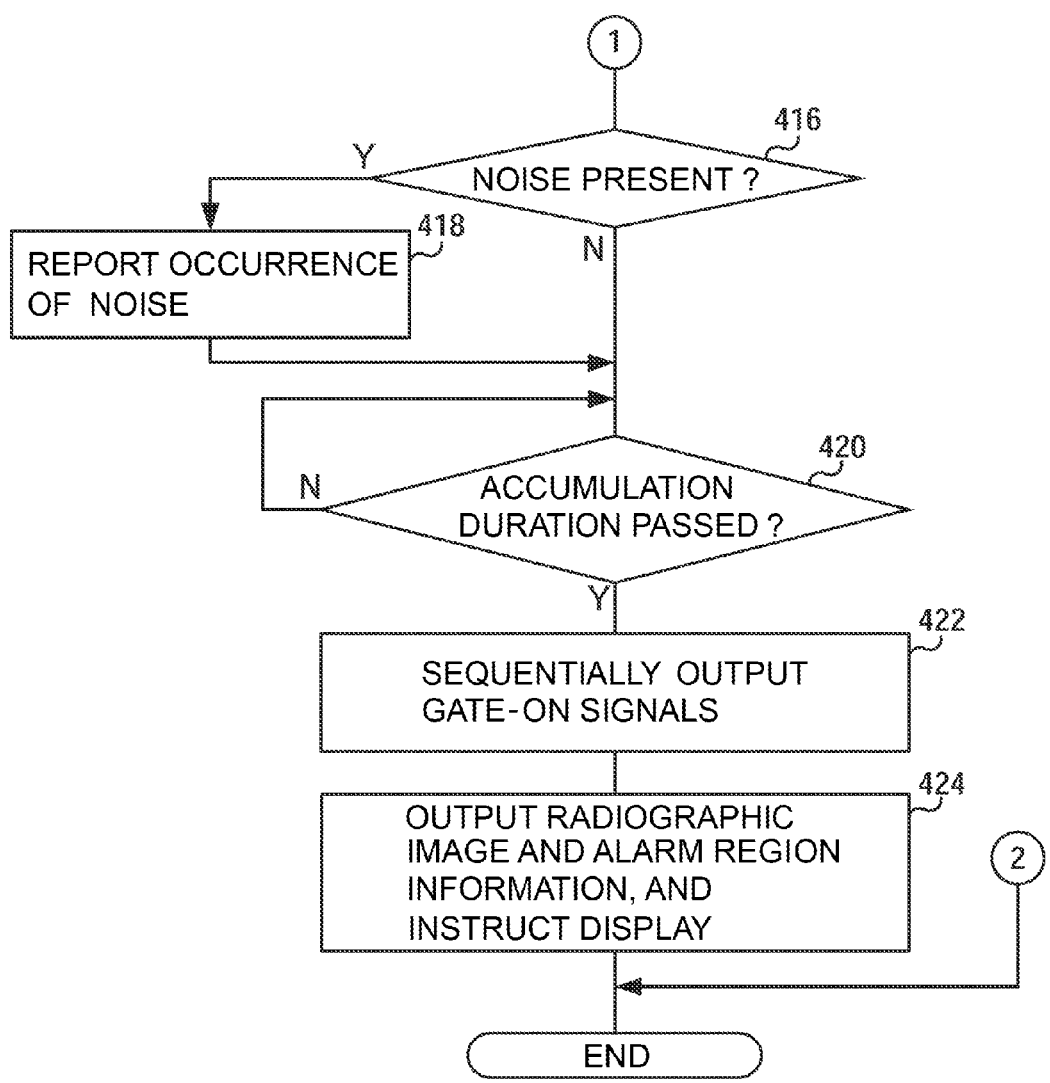

FIGS. 17A and 17B show a flowchart of an example of a flow of overall radiation image capture processing in the radiographic image detector 100 according to the present exemplary embodiment. This processing includes steps (processing) substantially the same as the overall image capture processing of the radiographic image detector 100 of the first exemplary embodiment. Therefore, steps (processing) that are substantially the same are denoted thus and details thereof are not described.

Steps 400 to 403 of the image capture processing of the present exemplary embodiment correspond with steps 100 to 103, respectively, of the image capture processing of the first exemplary embodiment (see FIG. 7). When the capture of a radiographic image is instructed, driving of the amplifiers 52 of the amplification circuits 50 is begun. If the acquired electronic signals are equal to or above a first threshold, it is determined that an irradiation of radiation has begun, gate-off signals are outputted to the scan line driving circuit 104, and the accumulation of charges in the radiation image capturing pixels 20A is begun.

Step 404 corresponds with step 104 of the image capture processing of the first exemplary embodiment. In step 404, the acquisition of changes over time of the electronic signals outputted from the radiation detection pixels 20B to the signal lines 3 (and the amplification circuits 50) begins. Specifically, in the present exemplary embodiment, electronic signals outputted to one signal line 3 (D1) are acquired from the amplification circuit $50_1$. Similarly, electronic signals outputted to another signal line 3 (D2) are acquired from the amplification circuit $50_2$, electronic signals outputted to another signal line 3 (D3) are acquired from the amplification circuit $50_3$ and electronic signals outputted to another signal line 3 (D4) are acquired from the amplification circuit $50_4$.

Next, step 406 corresponds with step 106 of the image capture processing of the first exemplary embodiment. A determination is made as to whether a predetermined duration has passed. If the predetermined duration has not passed, the acquisition of changes over time of the electronic signals from each signal line 3 continues. However, if the predetermined duration has passed, the acquisition of changes over time of the electronic signals stops and the control section 106 proceeds to step 408.

Figure 18:
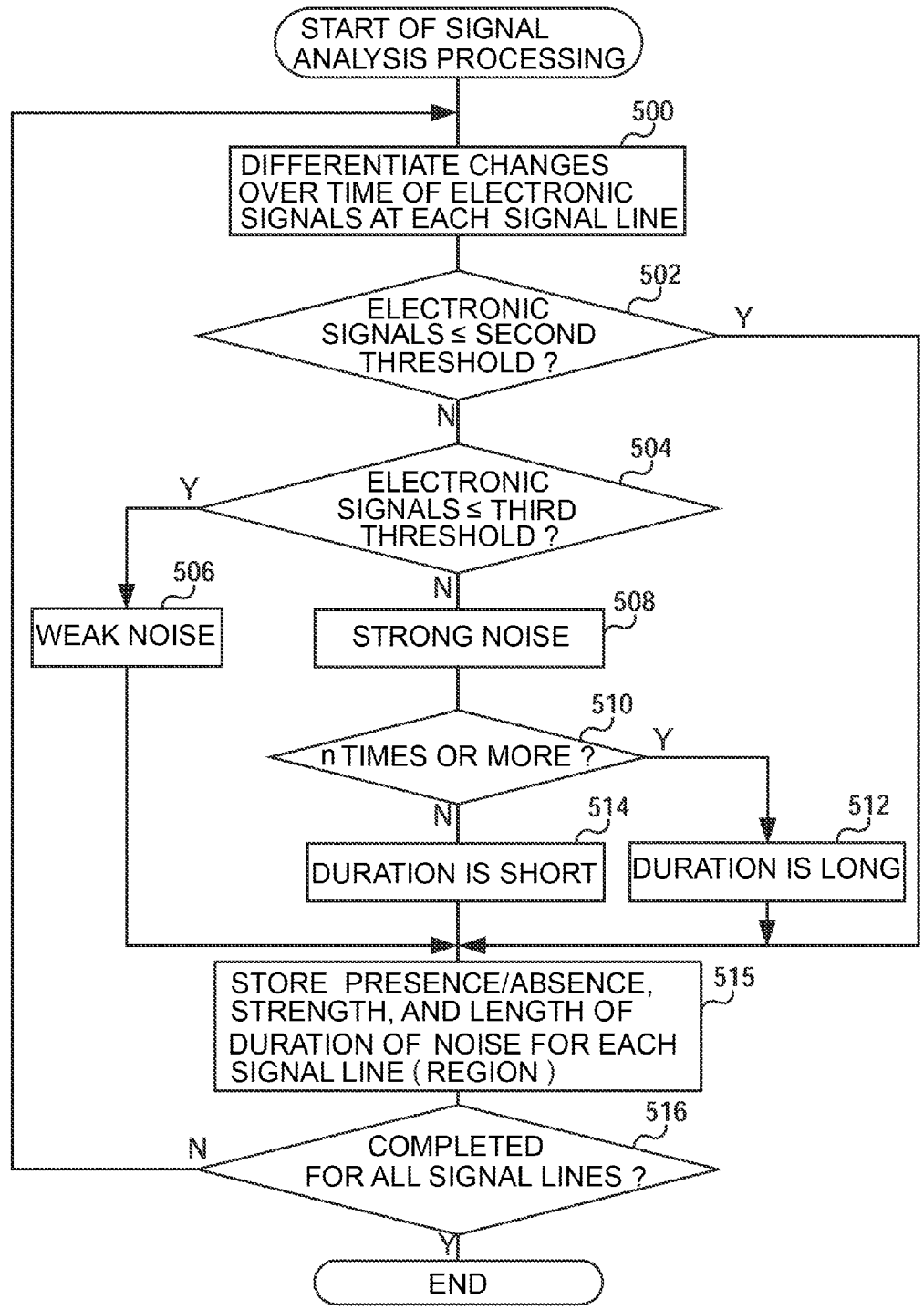
FIG. 18 is a flowchart of an example of signal analysis processing in the radiation image capturing device in accordance with the third exemplary embodiment.

Step 408 corresponds with step 108 of the image capture processing of the first exemplary embodiment. The presence or absence, strength and duration of noise are detected by signal analysis processing for each signal line 3 (regions to which the signal lines 3 correspond). FIG. 18 shows a flowchart of a specific example of flow of the signal analysis processing of the present exemplary embodiment. The present signal analysis processing corresponds to the signal analysis processing of the first exemplary embodiment (see FIG. 10). A case in which differentiation processing is applied to the changes over time of the electronic signals is illustrated here but, as in the signal analysis processing of the second exemplary embodiment (see FIG. 14), differences from moving averages of the changes over time of the electronic signals may be used.

Steps 500 to 514 of the signal analysis processing of the present exemplary embodiment perform processing corresponding to steps 200 to 214, respectively, of the signal analysis processing of the first exemplary embodiment, except that step 500 differentiates the changes over time of the respective electronic signals of the signal lines 3. The changes over time of the electronic signals from one signal line 3 are differentiated, and if the strength of the differentiated electronic signals (hereinafter referred to simply as electronic signals) is at or below the second threshold, it is determined that no noise is occurring and the control section 106 proceeds to step 515. However, if the strength of the electronic signals exceeds the second threshold, noise is occurring. Therefore, the strength of the electronic signals is compared with the third threshold, and if the strength is at or below the third threshold, it is determined that the noise has a low strength and the control section 106 proceeds to step 515. However, if the strength exceeds the third threshold, it is determined that the noise is strong. Then, if the number of occurrences is at or above n, it is determined that the duration is long, and if the number of occurrences is less than n, it is determined that the duration is short and the control section 106 proceeds to step 515.

In step 515, the presence/absence, strength/weakness, and length/shortness of duration of the noise is recorded for each signal line 3. In the present exemplary embodiment, the presence/absence, strength/weakness, and length/shortness of duration of the noise is recorded in respective regions corresponding to the signal lines 3 (regions that are defined by the pixels 20 from which the electronic signals are outputted to the signal lines 3).

Then, in step 516, a determination is made as to whether the detection and recording of the presence/absence, strength/weakness, and length/shortness of duration of noise has been completed for all the signal lines 3. If this has not been completed, the result of the determination is negative and the control section 106 returns to step 500 and repeats the present signal analysis processing. On the other hand, if this has been completed, the result of the determination is affirmative and the present signal analysis processing ends.

Hence, when the signal analysis processing ends, the control section 106 of the radiographic image detector 100 proceeds to step 410. In step 410 of the image capture processing of the present exemplary embodiment, a determination is made, on the basis of the results of the above-described signal analysis processing, as to whether there is a region in which noise with a high strength and a long duration occurs. If there is no region in which high-strength, long-duration noise occurs, the result of the determination is negative, it is determined that the radiographic image should be displayed, and the control section 106 proceeds to step 416. On the other hand, if there is a region in which high-strength, long duration noise occurs, the result of the determination is affirmative and the control section 106 proceeds to step 411.

In step 411, a determination is made as to whether or not the number of regions in which noise occurs is at or above a fourth threshold. In the first exemplary embodiment and the second exemplary embodiment, control is performed so as not to display a radiographic image if the strength of detected noise is high and the duration is long. In the present exemplary embodiment, however, even if the strength of noise is high and the duration is long, control is performed so as to display the radiographic image if a number of regions in which this noise occurs is small. Accordingly, in the radiographic image detector 100 of the present exemplary embodiment, the fourth threshold value for determining whether or not to display an image is specified in advance. The fourth threshold is found by prior testing and the like of numbers of regions with which noise is unlikely to be visible, numbers of regions with which noise is unlikely to be a problem even if visible, and the like. The fourth threshold may be set on this basis, and may be specified by a user.

In step 411, if the number of regions is less than the fourth threshold, the result of the determination is negative, it is determined that the radiographic image should be displayed, and the control section 106 proceeds to step 416. On the other hand, if the number of regions is equal to or greater than the fourth threshold, the result of the determination is affirmative, it is determined that the radiographic image should not be displayed, and the control section 106 proceeds to step 412.

Figure 19A:
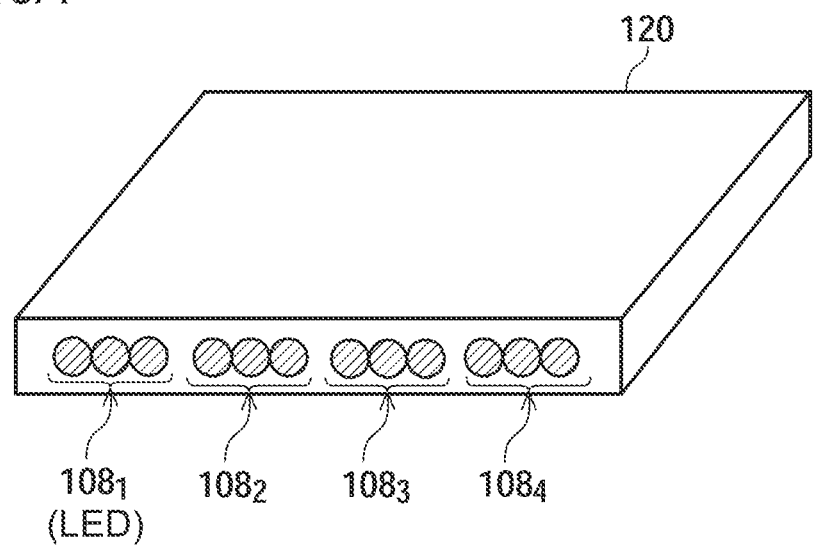
FIG. 19A is a descriptive diagram for describing the external appearance of a radiation detector in accordance with the third exemplary equipment.
Figure 19B:
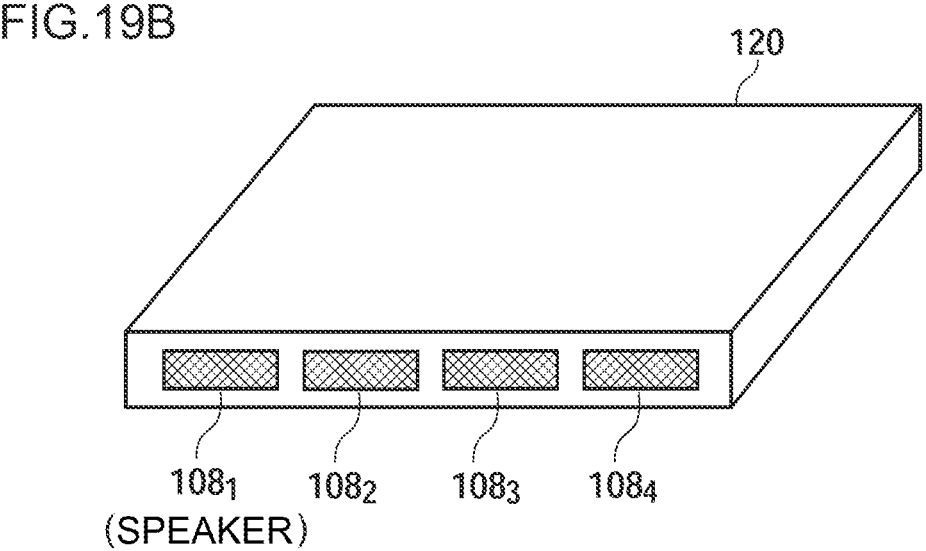
FIG. 19B is a descriptive diagram for describing the external appearance of a radiation detector in accordance with the third exemplary equipment.

Step 412 corresponds to step 112 of the image capture processing of the first exemplary embodiment, and notifies a user with the reporting section 108 that noise with a high strength and a long duration has been detected. A method of reporting to the user may be similar to the first exemplary embodiment, but reporting that indicates the regions in which noise has been detected is preferable. In the radiographic image detector 100 of the present exemplary embodiment, the reporting section 108 is plurally provided such that the reporting may indicate the regions in which noise has been detected. FIG. 19A and FIG. 19B show examples of the appearance of the radiographic image detector 100 (the casing 120) of the present exemplary embodiment. FIG. 19A shows a case in which each reporting section 108 is LEDs, and corresponds to FIG. 3A of the first exemplary embodiment. FIG. 19B shows a case in which each reporting section 108 is a speaker, and corresponds to FIG. 3B of the first exemplary embodiment. As shown in FIG. 19A and FIG. 19B, in the present exemplary embodiment, the reporting sections 108 are provided at positions corresponding with the respective regions. Each reporting section 108 corresponding to the position of a region at which noise has been detected gives a report relating to the detected noise to the user, similarly to the first exemplary embodiment. With the radiographic image detector 100 (casing 120) shown in FIG. 19A and FIG. 19B, the reporting section $108_1$ corresponds with a region corresponding to a signal line 3 (D1), the reporting section $108_2$ corresponds with a region corresponding to another signal line 3 (D2), the reporting section $108_3$ corresponds with a region corresponding to another signal line 3 (D3) and the reporting section $108_4$ corresponds with a region corresponding to another signal line 3 (D4). For example, if it is detected that noise with a high strength and a long duration has occurred in electronic signals outputted to the signal line 3 (D1) and in electronic signals outputted to the signal line 3 (D2), reports indicating that high-strength, long duration noise has been detected are given by the reporting section $108_1$ and the reporting section $108_2$.

Step 414 corresponds to step 114 of the image capture processing of the first exemplary embodiment. The control section 106 instructs the output of driving signals that are gate-on signals, and resets the charges accumulated at the radiation image capturing pixels 20A, then the present processing ends.

If it is determined that the radiographic image should be displayed, steps 416 to 424 correspond to steps 116 to 124, respectively, of the image capture processing of the first exemplary embodiment. A determination is made as to whether there are regions in which noise has been detected, and if there is a region in which noise has been detected, the detection of the noise and the detected region(s) are reported. In the present exemplary embodiment, reports are given in accordance with types (strength and length) of detected noise in the same manner as in the first exemplary embodiment. The reports indicating the regions in which noise is detected are given in the same manner as in the above-described step 412.

When the charge accumulation duration for capturing the radiographic image has passed, the control section 106 instructs the sequential output of driving signals that are gate-on signals to each of the scan lines 101, and the electronic signals are acquired in accordance with the charges accumulated at the radiation image capturing pixels 20A. The control section 106 generates the radiographic image on the basis of the acquired electronic signals. In step 424 of the present exemplary embodiment, the control section 106 outputs the generated radiographic image to the control device 202, and outputs information indicating regions in which noise is detected (alarm regions for warning a user) to the control device 202. After the radiographic image and information concerning alarm regions have been outputted to the control device 202 to be displayed, the present processing ends.

Figure 20:
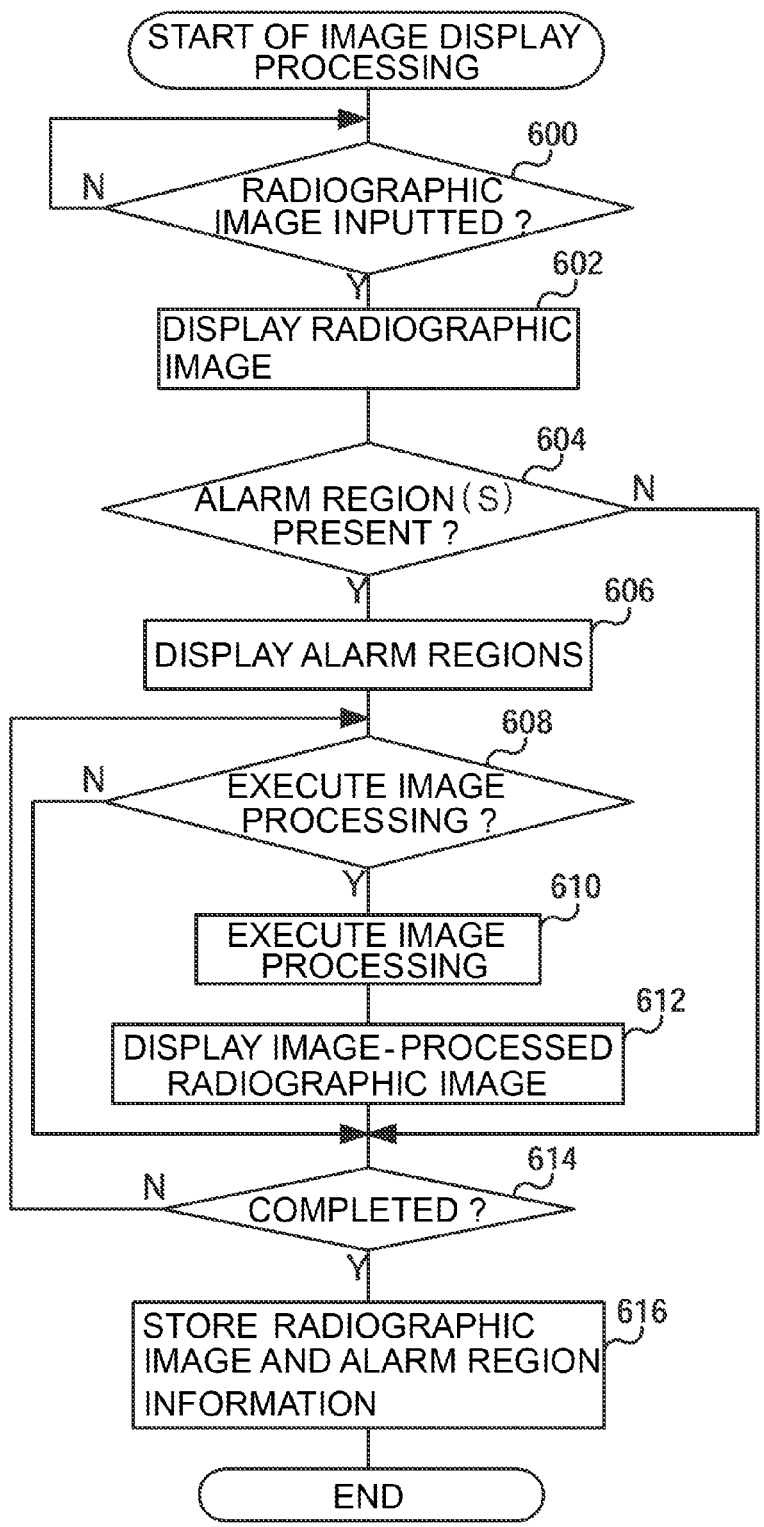
FIG. 20 is a flowchart of an example of radiographic image image display processing in a control device of a radiation image capturing device in accordance with the third exemplary embodiment.

At the control device 202 of the present exemplary embodiment, the radiographic image is displayed in accordance with an instruction to display the radiographic image and information concerning alarm regions that have been outputted from the radiographic image detector 100 in this manner. FIG. 20 shows a flowchart of an example of radiographic image image display processing that is executed by the control device 202 of the present exemplary embodiment. In the present exemplary embodiment, the present processing is executed by the control section 210 of the control device 202 when radiographic image capture is instructed.

In step 600, a determination is made as to whether a radiographic image (i.e., electronic signals representing the radiographic image) has been inputted. If a radiographic image has not been inputted, the result of the determination is negative and the control section 210 is in a standby state. On the other hand, if a radiographic image has been inputted by step 424 of the image capture processing described above, the result of the determination is affirmative and the control section 210 proceeds to step 602. In step 602, the inputted radiographic image is displayed at the display section 212. FIG. 21 shows a specific example of display of a radiographic image in the present exemplary embodiment. As shown in FIG. 21, in the present exemplary embodiment, a radiographic image 60, alarm region display portions 62, an instruction portion 64 and an instruction portion 66 are displayed at the display section 212. The alarm region display portions 62 ($62_1$ to $62_4$) indicate alarm regions. The instruction portion 64 is for a user to instruct the execution of image processing on the displayed radiographic image.

The radiographic image 60 corresponds to the radiographic image inputted from the radiographic image detector 100. FIG. 21 illustrates a case of displaying the radiographic image 60 with noise N included. The alarm region display portions 62 are not particularly limited, provided the inputted alarm region locations may be displayed to be recognizable to a user. In the present exemplary embodiment, as a specific example as shown in FIG. 21, the alarm region display portion $62_1$ to alarm region display portion $62_4$ corresponding to the respective regions are provided, and those at alarm regions light up or flash. FIG. 21 illustrates a case in which noise (see noise N) is detected in the region corresponding to a signal line 3 (D2), so this is an alarm region and the alarm region display portion $62_2$ is lit up.

The instruction portion 64 is used in a case in which a user instructs the execution of image processing for removing noise N from the displayed radiographic image 60 (which is described in detail below). The instruction portion 66 is used in a case in which a user instructs the end of display of the radiographic image 60.

When the radiographic image 60 is displayed, in step 604, a determination is made as to whether there is an alarm region. If there is no alarm region, the result of the determination is negative and the control section 210 proceeds to step 614. Alternatively, if there is an alarm region, the result of the determination is affirmative and the control section 210 proceeds to step 606. In step 606, the alarm regions are indicated by the alarm region display portions 62 (see FIG. 21).

Then, in step 608, a determination is made as to whether the image processing for removing the noise N is to be executed. If execution of the image processing is not instructed by a user, via the instruction portion 64, the result of the determination is negative and the control section 210 proceeds to step 614. Alternatively, if execution of the image processing is instructed, the result of the determination is affirmative and the control section 210 proceeds to step 610. In step 610, the image processing for removing the noise N is executed on the radiographic image 60 (i.e., image information corresponding to the radiographic image 60). This image processing is not particularly limited; it is sufficient if suitable filter processes and the like for removing the noise N are determined by prior testing and the like. Then, in step 612, the image-processed radiographic image 60 is displayed at the display section 212.

In step 614, a determination is made as to whether to end the display of the radiographic image 60. If ending the display has not instructed by a user via the instruction portion 66, the result of the determination is negative, the control section 210 proceeds to step 608, and the present processing is repeated. However, if ending the display has been instructed, the result of the determination is affirmative and the control section 210 proceeds to step 616. In step 616, the radiographic image 60 (i.e., image information corresponding to the radiographic image 60) and the information concerning the alarm regions are associated and stored, then the present processing ends. The radiographic image 60 that is stored may be the radiographic image 60 prior to the image processing of step 610, and may be the radiographic image 60 subsequent to the image processing. The storage location may be a storage portion of a memory or the like, which is not shown in the drawings, in the control device 202, and may be a storage portion outside the control device 202 (the radiographic image capturing device 201).

In the present exemplary embodiment, the control section 106 acquires the electronic signals outputted from each of the signal lines 3 (the amplification circuits 50), and detects the presence or absence, strength and length of duration of noise in the respective acquired electronic signals. Consequently, locations (regions) at which noise is detected may be made apparent to a user. Moreover in the present exemplary embodiment, the radiographic image 60 is displayed in accordance with a number of regions in which noise is detected. If the number of regions is small, the radiographic image 60 is displayed. If the number of regions in which noise is detected is small, display of the radiographic image 60 is prioritized over repeating image capture, and the radiographic image 60 may be checked by a user. Therefore, the burden of repeating image captures may be moderated.

Fourth Exemplary Embodiment

Next, a fourth exemplary embodiment is described. The present exemplary embodiment has structures and operations substantially the same as in the third exemplary embodiment, so portions that are the same are not described. In the third exemplary embodiment, if the number of regions in which noise is detected (alarm regions) is small, control is performed to display the radiographic image 60. However, the radiographic image detector 100 of the present exemplary embodiment is constituted to perform control so as to display the radiographic image 60 depending on the locations of alarm regions.

Figure 22A:
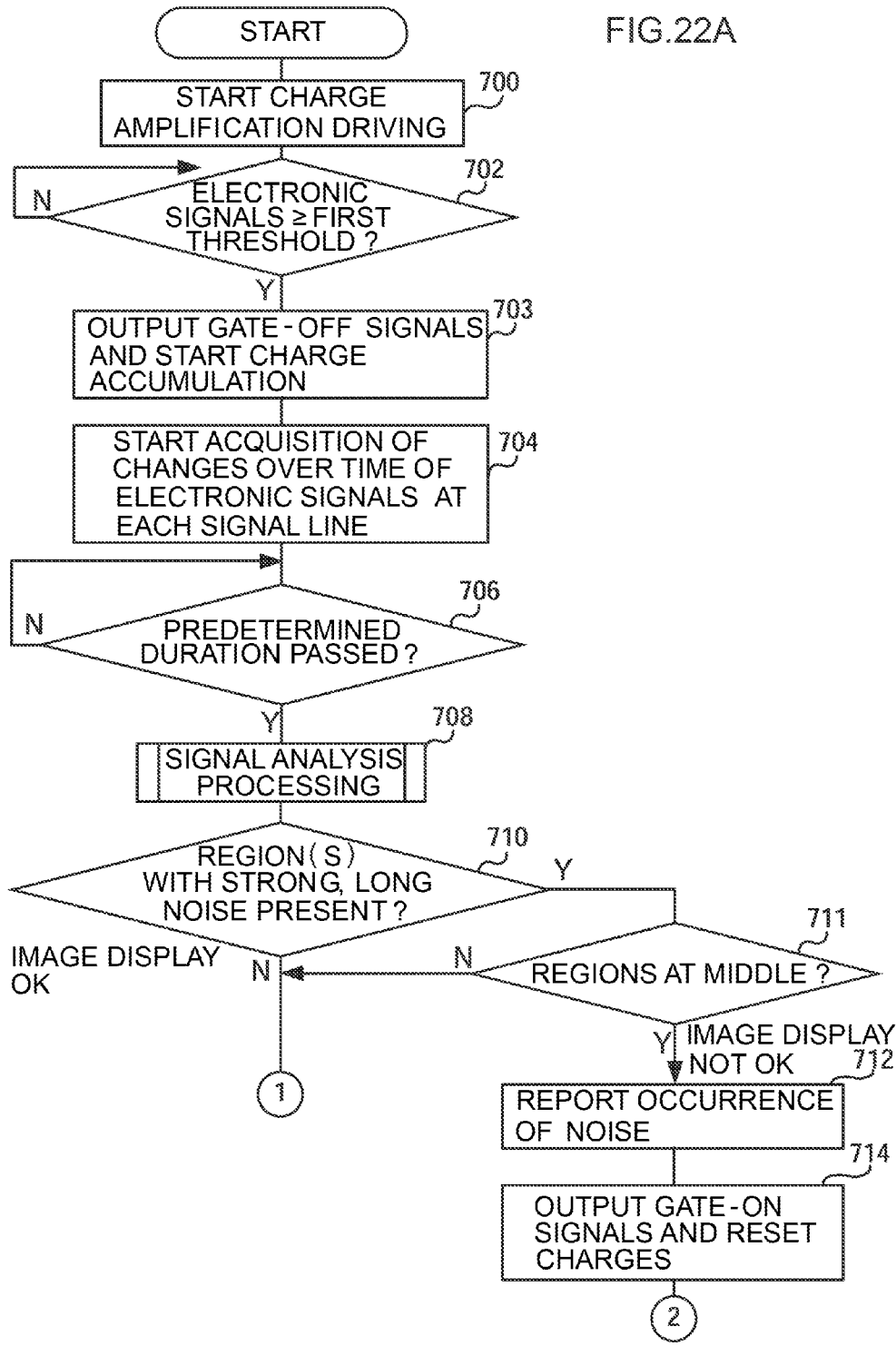
FIGS. 22A and 22B are a flowchart of an example of radiation image capture processing in a radiation image capturing device in accordance with a fourth exemplary embodiment.
Figure 22B:
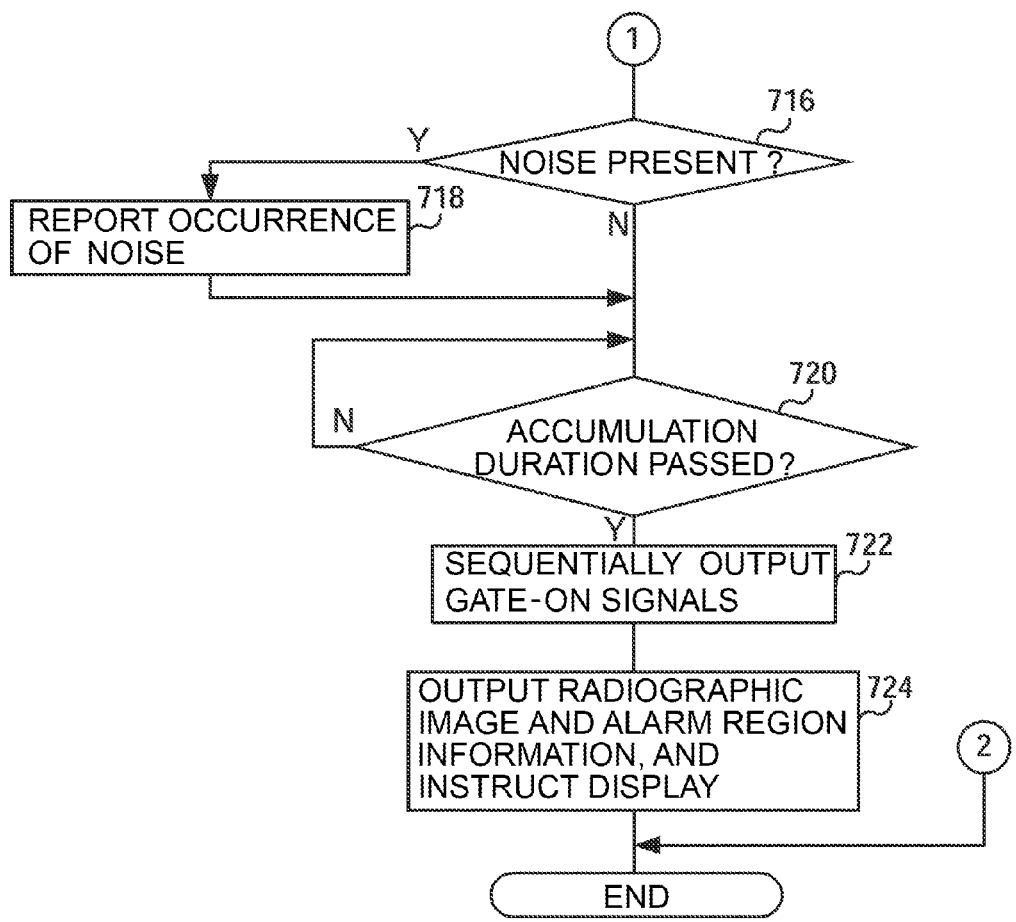

FIGS. 22A and 22B show a flowchart of an example of flow of the overall radiation image capture processing of the radiographic image detector 100 of the present exemplary embodiment. The present processing includes steps (processing) substantially the same as the overall image capture processing of the radiographic image detector 100 of the third exemplary embodiment (FIG. 17). Therefore, steps (processing) that are substantially the same are denoted thus and details thereof are not described.

Steps 700 to 724 of the image capture processing of the present exemplary embodiment correspond with steps 400 to 424, respectively, of the image capture processing of the third exemplary embodiment (see FIG. 17). In the present exemplary embodiment, the processing of step 711 differs from step 411 of the image capture processing of the third exemplary embodiment, so this processing is described in detail.

If it is determined in step 710 that there is a region in which noise with a high strength and a long duration has been detected, in step 711, a determination is made as to whether the location of a region in which noise has been detected is at the middle of the radiographic image 60. The "middle of the radiographic image 60" in the present exemplary embodiment is defined in advance from regions according to the radiographic image 60 or regions specified by a user. In general, important images such as regions of interest that should be observed by a user and the like are displayed close to the middle of the radiographic image 60. Meanwhile, there are few cases in which important regions are displayed at the periphery of the radiographic image 60 and there are many cases in which there is no problem if noise is generated at regions at the periphery. Therefore, in the present exemplary embodiment, the middle of the radiographic image 60 at which important images will be displayed is found by prior testing and the like, or is specified by a user. If noise with a high strength and a long duration is detected at the middle of the radiographic image 60, control is performed such that the radiographic image 60 is not displayed. However, even if there is noise with a high strength and a long duration, if the noise is at the periphery (regions excluding the middle), control is performed to report the fact that noise has been detected to warn the user, and to display the radiographic image 60.

In a case in which the aforementioned middle of the radiographic image 60 is specified by a user, as an example, a constitution is possible in which instruction portions corresponding to the alarm regions are provided together with the alarm region display portions 62 shown in FIG. 21. Thus, locations at which noise is permitted to occur and locations at which noise must not occur may be designated by the user. In the present exemplary embodiment, the "middle" is referred to for convenience of description but, obviously, all regions of the radiographic image 60 (specifically, all alarm regions) may be specified by a user, such that it may be specified that the radiographic image 60 will be displayed regardless of the locations of regions in which noise occurs. In a case in which urgent display of the radiographic image 60 is required, in an emergency or the like, it is preferable to prioritize display of the radiographic image 60 regardless of types, locations and the like of noise in this manner.

If it is determined in step 711 that the location of a region in which noise has occurred is at the middle of the radiographic image 60, the control section 106 proceeds to step 712 and performs processing from step 712 onward, it having been determined that the radiographic image 60 should not be displayed. On the other hand, if it is determined that there is no such region at the middle, the control section 106 proceeds to step 716 and performs processing from step 716 onward, it having been determined that the radiographic image 60 should be displayed. If the radiographic image 60 is displayed, similarly to the third exemplary embodiment, the control section 106 instructs that the radiographic image 60 be displayed at the display section 212 of the control device 202 such that types (the strength and length) of detected noise and alarm regions are recognizable to a user, then the present processing ends.

In the present exemplary embodiment, if noise with a high strength and a long duration is detected, the control section 106 performs control to display the radiographic image 60 depending on the locations of regions in which the noise is detected. Therefore, the display of the radiographic image 60 may be prioritized if no region in which noise is detected is a region in which an important image is to be displayed. Furthermore, the locations (regions) at which noise is detected may be made apparent to the user. Moreover, in the present exemplary embodiment, display of the radiographic image 60 regardless of detections of noise may be prioritized.

The above-described third exemplary embodiment and fourth exemplary embodiment may be combined, and whether the radiographic image 60 is displayed or not may be controlled in accordance with the number and locations of regions in which noise with a high strength and a long duration occurs. Further, similarly to the third exemplary embodiment and the fourth exemplary embodiment, even if the strength of detected noise is weak and/or the duration is short, whether the radiographic image 60 is displayed or not may be controlled in accordance with the number and locations of regions in which the noise is detected.

In the third exemplary embodiment and the fourth exemplary embodiment, changes over time of the electronic signals are acquired for each of the signal lines 3 (the amplification circuits 50), but this is not limiting. Changes over time of the electronic signals may be acquired for each of a plural number (a predetermined number) of the signal lines 3 (the amplification circuits 50), and the above-described control processing may be performed for the regions corresponding to the plural numbers of signal lines 3.

In the radiographic image detector 100 of the third exemplary embodiment and the fourth exemplary embodiment, as shown in FIG. 16, the radiation detection pixels 20B are provided on all of the signal lines 3. However, even if the radiation detection pixels 20B are provided on some of the signal lines 3 as in the radiographic image detector 100 of the first exemplary embodiment (see FIG. 2), the above-described control processing may be performed for each of the signal lines 3 at which the radiation detection pixels 20B are provided.

Fifth Exemplary Embodiment

Next, a fifth exemplary embodiment is described. In the present exemplary embodiment, structures and operations that are substantially the same as in the above exemplary embodiments are not described. The radiographic image detector 100 of the present exemplary embodiment has a method of detecting the start of irradiation of radiation that is different from the above exemplary embodiments. Therefore, the method of detecting the start of irradiation of radiation is described.

Figure 23:
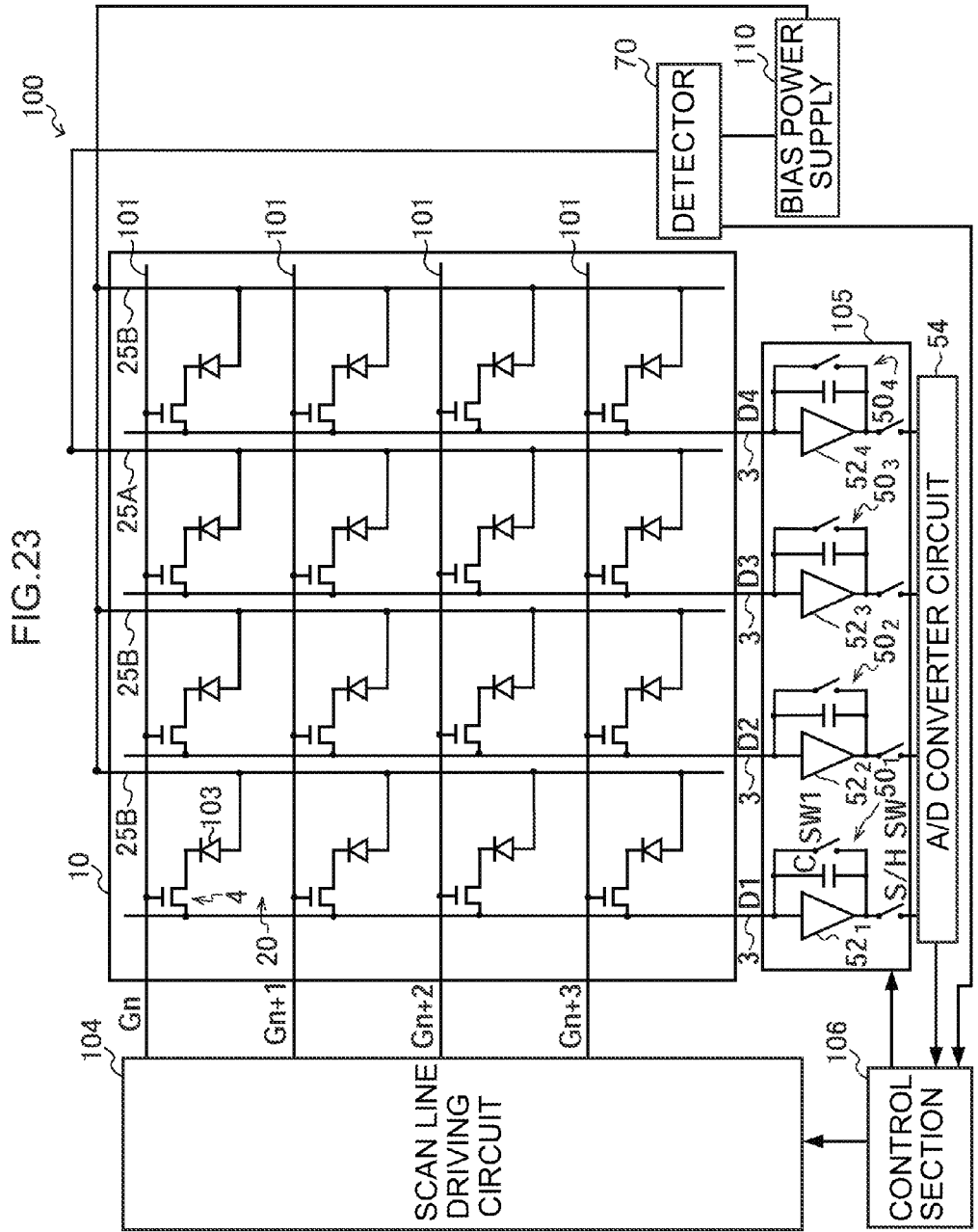
FIG. 23 is a structural diagram showing an example of overall structure of a radiographic image detector in accordance with a fifth exemplary embodiment.
Figure 24:
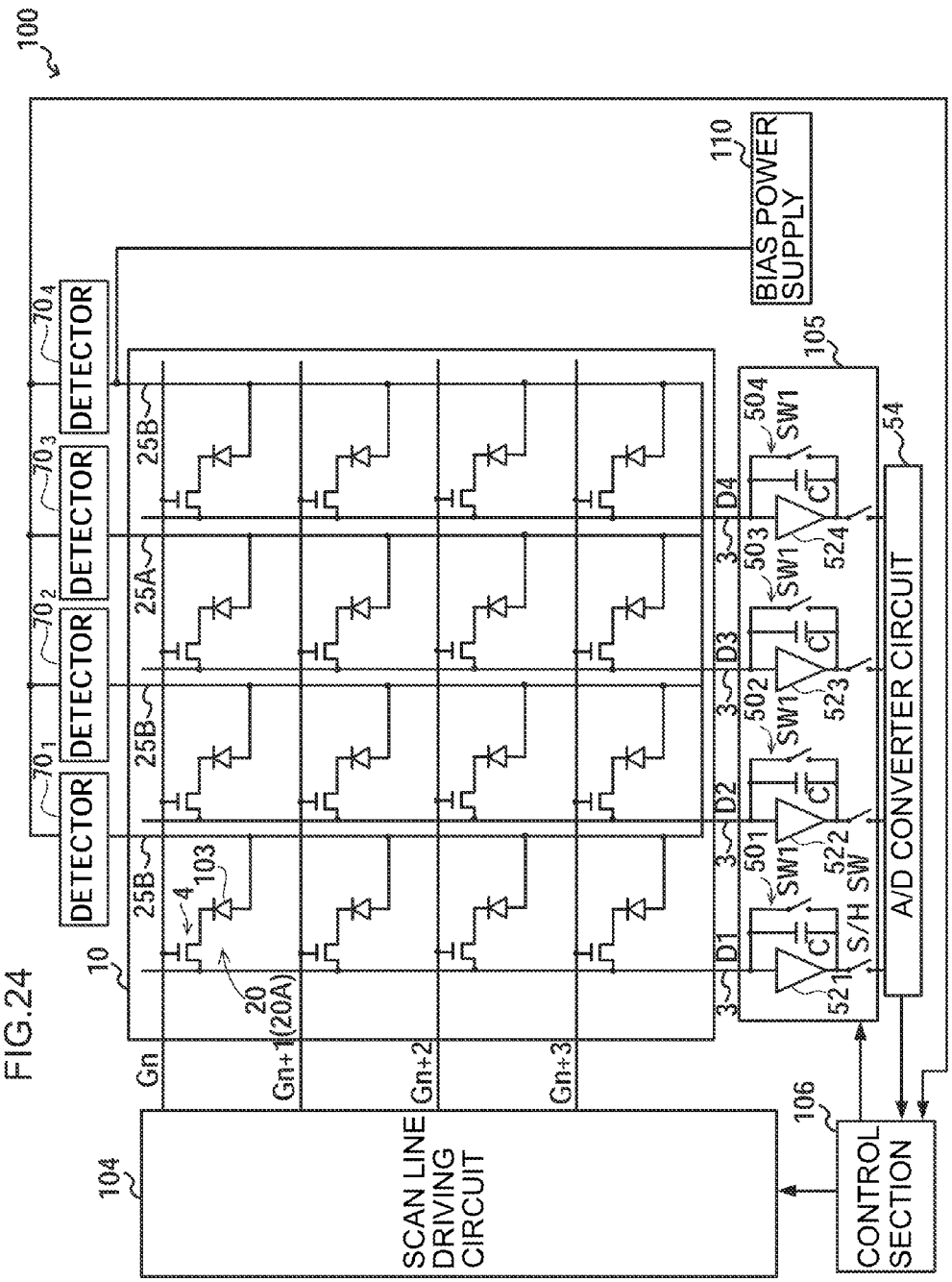
FIG. 24 is a structural diagram showing another example of overall structure of a radiographic image detector in accordance with the fifth exemplary embodiment.

In the radiographic image detector 100 of the present exemplary embodiment, charges flowing into the bias lines 25 are detected by a detector 70, and the start of irradiation of radiation is detected by the control section 106 on the basis of the detected charges and a threshold. FIG. 23 shows a structural diagram showing an example of overall structure of the radiographic image detector 100 of the present exemplary embodiment. FIG. 24 shows a structural diagram showing another example of overall structure of the radiographic image detector 100 of the present exemplary embodiment. In the radiographic image detector 100 shown in FIG. 23, of the bias lines 25, a bias line 25A is connected to the detector 70. Charges flowing into the bias line 25A are detected by the detector 70, and the control section 106 detects the start of irradiation of radiation on the basis of the detected charges and the threshold. In contrast, in the radiographic image detector 100 shown in FIG. 24, the detector 70 is provided for each of the bias lines 25 (detectors $70_1$ to $70_4$). Charges flowing into the bias lines 25 are detected by the detectors 70, and the control section 106 detects the start of irradiation of radiation on the basis of the detected charges and the threshold. Note that providing the detector 70 for each of the bias lines 25 as in the radiographic image detector 100 shown in FIG. 24 may improve accuracy of detection, with determinations being possible in accordance with the respective regions, so is preferable.

The method of detecting the start of irradiation of radiation of the present exemplary embodiment is now described. In the present exemplary embodiment, processing is substantially the same as in the image capture processing of the first exemplary embodiment, apart from the processing of steps 100 and 102 for detecting the start of irradiation of radiation (see FIG. 7), so is not described.

Figure 25:
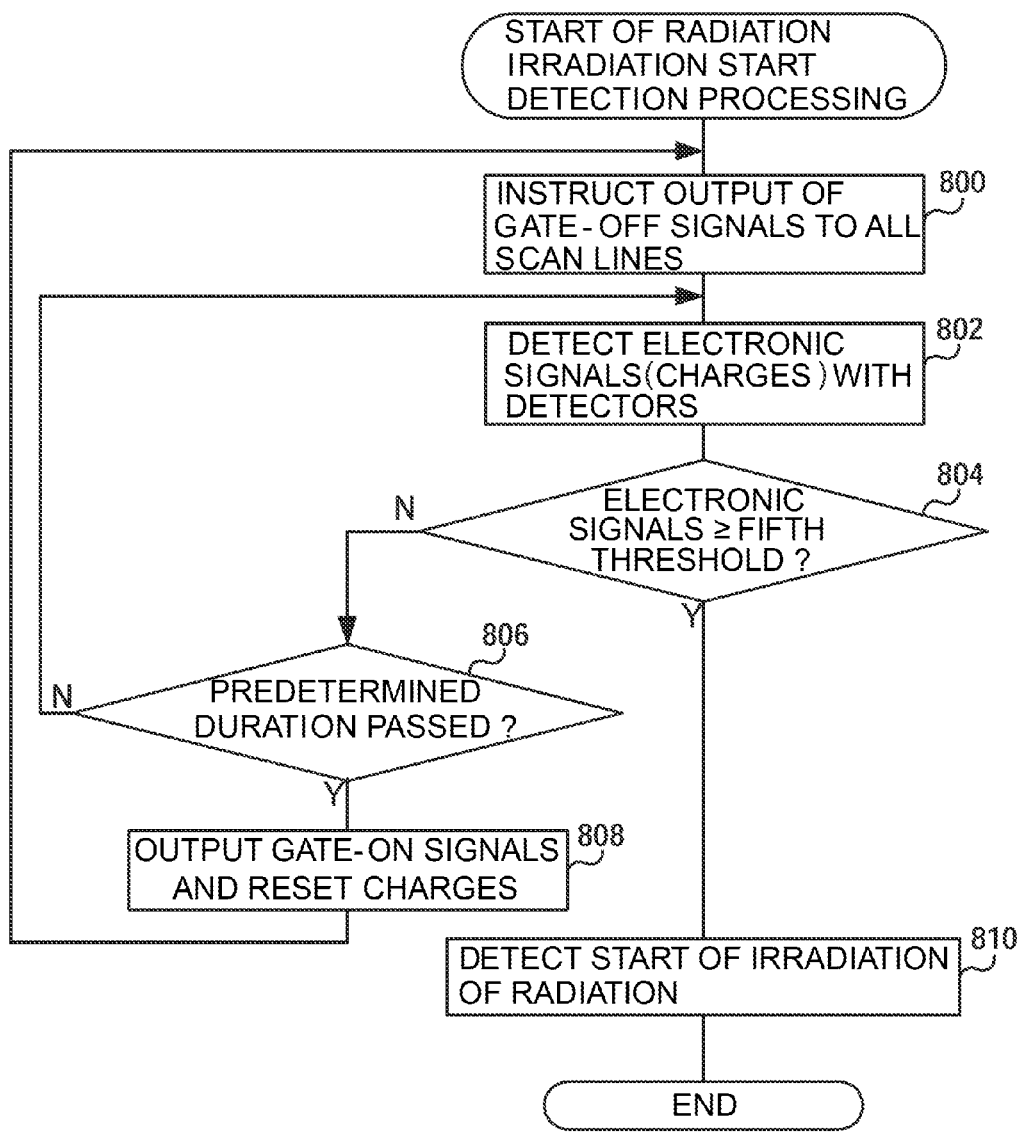
FIG. 25 is a flowchart of an example of radiation irradiation start detection processing in a radiation image capturing device in accordance with the fifth exemplary embodiment.

FIG. 25 shows a flowchart of an example of radiation irradiation start detection processing of the present exemplary embodiment.

In step 800, the scan line driving circuit 104 is instructed to output gate-off signals to all the scan lines 101. Thus, gate-off signals are outputted from the scan line driving circuit 104 to the pixels 20, and the TFT switches 4 of all the pixels 20 are turned Off.

Then, in step 802, electronic signals (charges) flowing along the bias line(s) 25 are detected by the detector(s) 70, and in step 804 a determination is made as to whether or not the detected electronic signals are equal to or greater than a fifth threshold. The fifth threshold value may be found as a threshold for the start of irradiation of radiation by prior testing and the like. If the radiographic image detector 100 is provided with a detector 70 for each of the bias lines 25 as shown in FIG. 24, a determination may be made as to whether or not the electronic signals detected by at least a predetermined number of the detectors 70 are at or above the fifth threshold, or a determination may be made as to whether or not the electronic signals detected by all the detectors 70 are at or above the fifth threshold. Which of these is set is not particularly limited, and may be set in advance in accordance with usage, imaging and the like of the radiographic image detector 100.

If the electronic signals are below the fifth threshold, the result of the determination is negative and the control section 106 proceeds to step 806. In step 806, a determination is made as to whether a predetermined duration for a charge reset has passed. In the case of the present exemplary embodiment, the TFT switches 4 are turned off by the gate-off signals. Consequently, charges are accumulated at all the pixels 20. If the accumulated charges are not reset, electronic signals that cause noise will increase and the dynamic range will be smaller, and image quality of the radiographic image will be lower. Therefore, in the present exemplary embodiment, control is performed so as to reset the charges accumulated at the pixels 20 at intervals of the predetermined duration. Note that the predetermined duration may be found by prior testing and the like in accordance with the radiographic image detector 100, the pixels 20 and the like.

If the predetermined duration has not passed, the result of the determination is negative, the control section 106 returns to step 802, and the present processing is repeated. However, if the predetermined duration has passed, the result of the determination is affirmative and the control section 106 proceeds to step 808. In step 808, operations by the detector(s) 70 for detecting the start of irradiation of radiation are temporarily suspended, and the scan line driving circuit 104 is instructed to output gate-on signals to all the scan lines 101. By this instruction, driving is performed so as to reset the charges accumulated at all the pixels 20. After the reset of the charges, the control section 106 returns to step 800 and the operations for detecting the start of irradiation of radiation are restarted.

Meanwhile, in step 804, if the electronic signals are equal to or greater than the fifth threshold, the result of the determination is affirmative and the control section 106 proceeds to step 810, the start of irradiation of the radiation is detected, and the present processing ends.

In the present exemplary embodiment, the detection of the charges (electronic signals) flowing in the bias line(s) 25 by the detector(s) 70, the comparison of the electronic signals with the fifth threshold, and the detection of the start of irradiation of radiation if the electronic signals are equal to or greater than the fifth threshold are carried out in the state in which gate-off signals have been outputted to the scan lines 101. Therefore, noise (for example, feed-through noise) that is caused by the output of gate-on signals to the scan lines 101 (the operation to turn the TFT switches 4 on) is not produced, and the signal-to-noise ratio may be improved.

Sixth Exemplary Embodiment

Next, a sixth exemplary embodiment is described. In the present exemplary embodiment, structures and operations that are substantially the same as in the above exemplary embodiments are not described. The radiographic image detector 100 of the present exemplary embodiment has a method of detecting the start of irradiation of radiation that is different from the above exemplary embodiments. Therefore, the method of detecting the start of irradiation of radiation is described.

Figure 26:
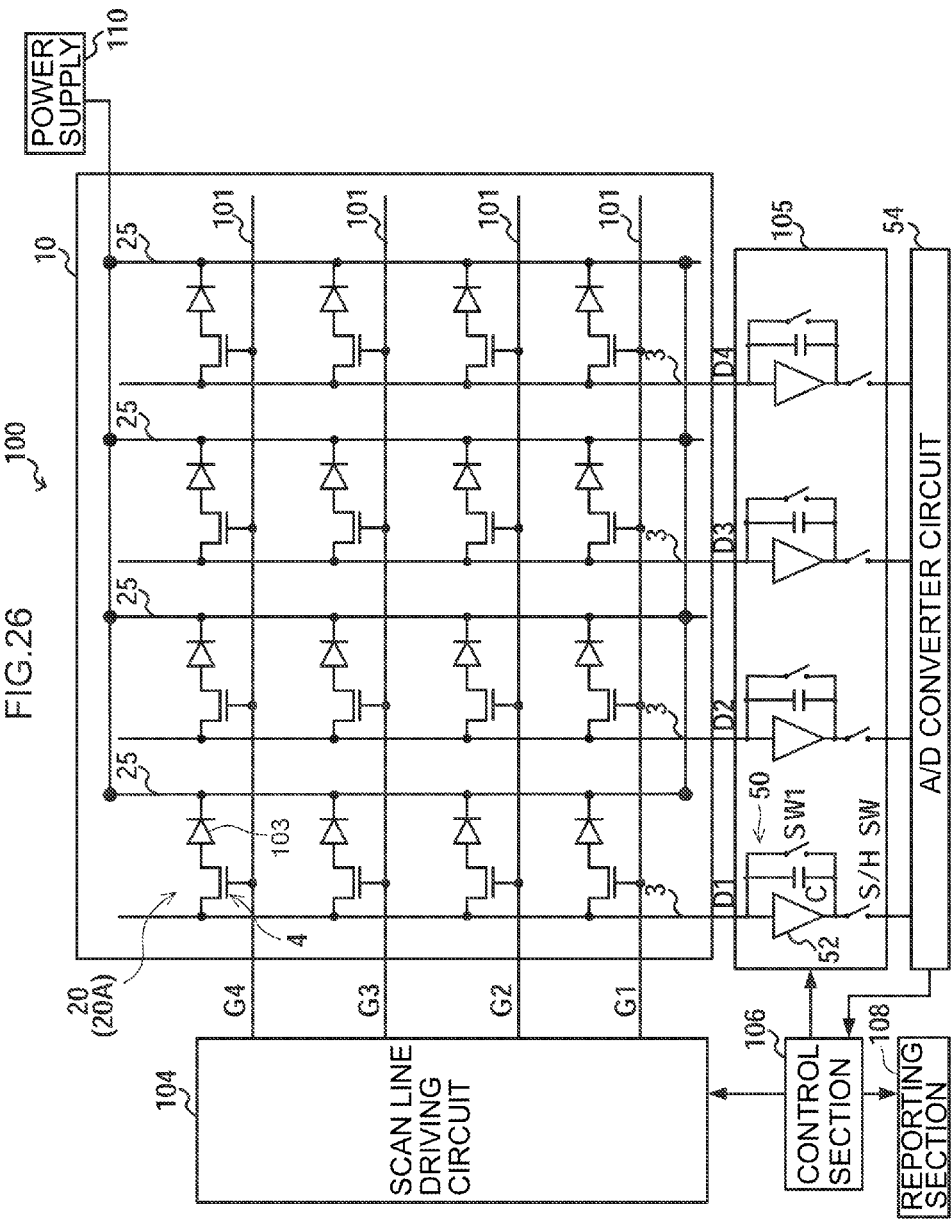
FIG. 26 is a structural diagram showing an example of overall structure of a radiographic image detector in accordance with a sixth exemplary embodiment.

In the radiographic image detector 100 of the present exemplary embodiment, the start of irradiation of radiation is detected by the control section 106 on the basis of currents (charges) leaking from the pixels 20 and a threshold value. FIG. 26 shows a structural diagram showing an example of overall structure of the radiographic image detector 100 of the present exemplary embodiment.

The method of detecting the start of irradiation of radiation of the present exemplary embodiment is now described. In the present exemplary embodiment, processing is substantially the same as in the image capture processing of the first exemplary embodiment, apart from the processing of steps 100 and 102 for detecting the start of irradiation of radiation (see FIG. 7), so is not described.

Figure 27:
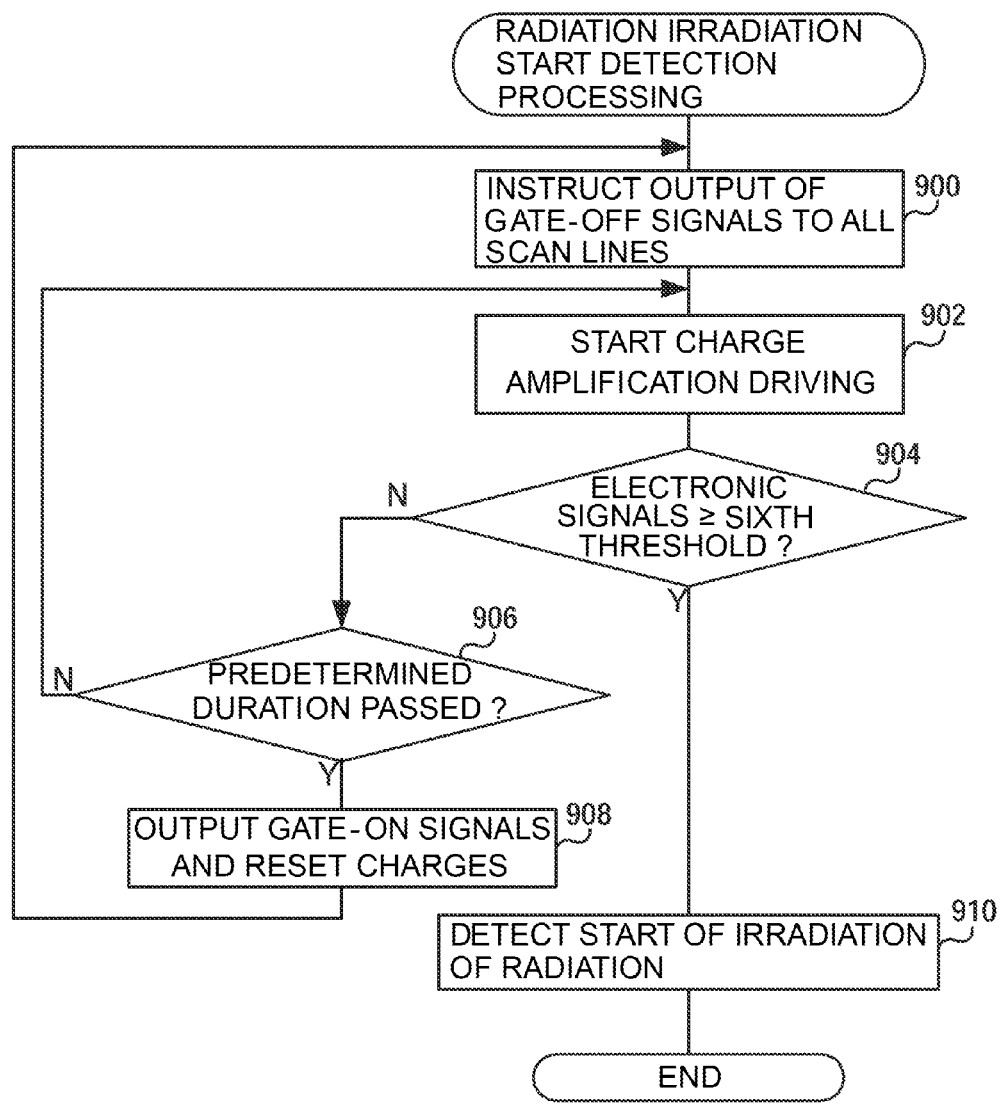
FIG. 27 is a flowchart of an example of radiation irradiation start detection processing in a radiation image capturing device in accordance with the sixth exemplary embodiment.

FIG. 27 shows a flowchart of an example of irradiation start detection processing of the present exemplary embodiment.

In step 900, similarly to the radiation irradiation start detection processing of the fifth exemplary embodiment, the scan line driving circuit 104 is instructed to output gate-off signals to all the scan lines 101. In response to this instruction, gate-off signals are outputted from the scan line driving circuit 104 to the pixels 20, and the TFT switches 4 of all the pixels 20 are turned off.

Then, in step 902, driving of the amplification circuits 50 (amplifiers 52) of the signal detection circuit 105 is started and the same are continuously driven. Even though the TFT switches 4 of the pixels 20 are in the Off state, leakage currents are produced in response to an irradiation of radiation, and charges (electronic signals) corresponding to the leakage currents flow in the signal lines 3 and are sampled by the amplification circuits 50 (amplifiers 52). Then, in step 904, the control section 106 compares electronic signals according to charges that are sampled by the amplification circuits 50 with a sixth threshold, and detects whether an irradiation of radiation has started from whether or not the electronic signals are equal to or greater than the sixth threshold. The sixth threshold value may be found as a threshold for the start of irradiation of radiation by prior testing and the like.

If the electronic signals are below the sixth threshold, the result of the determination is negative and the control section 106 proceeds to step 906. In step 906, a determination is made as to whether a predetermined duration for a charge reset has passed. In the case of the present exemplary embodiment, similarly to the fifth exemplary embodiment, the TFT switches 4 are turned Off by gate-off signals. Therefore, charges are accumulated at all the pixels 20. Consequently, if the accumulated charges are not reset, electronic signals that cause noise will increase and the dynamic range will be smaller, and image quality of the radiographic images will be lower. Therefore, in the present exemplary embodiment, control is performed so as to reset the charges accumulated at the pixels 20 at intervals of the predetermined duration. Note that the predetermined duration (which is generally different from the "predetermined duration" of the fifth exemplary embodiment) may be found by prior testing and the like in accordance with the radiographic image detector 100, the pixels 20 and the like.

If the predetermined duration has not passed, the result of the determination is negative, the control section 106 returns to step 904, and the present processing is repeated. However, if the predetermined duration has passed, the result of the determination is affirmative and the control section 106 proceeds to step 908. In step 908, operations by the signal detection circuit 105 for detecting the start of irradiation of radiation are temporarily suspended, and the scan line driving circuit 104 is instructed to output the gate-on signals to all the scan lines 101. In response to this instruction, driving is performed so as to reset the charges accumulated at all the pixels 20. After the reset of the charges, the control section 106 returns to step 900 and the operations for detecting the start of irradiation of radiation are restarted.

Meanwhile, in step 904, if the electronic signals are equal to or greater than the sixth threshold, the result of the determination is affirmative and the control section 106 proceeds to step 910, the start of irradiation of the radiation is detected, and the present processing ends.

In the present exemplary embodiment, the sampling by the amplification circuits 50 of the electronic signals according to the leakage currents flowing from the pixels 20 to the signal lines 3, the comparison of the sampled electronic signals with the sixth threshold, and the detection of irradiation of radiation, if the sampled electronic signals are equal to or greater than the sixth threshold, are carried out in the state in which the gate-off signals have been outputted to the scan lines 101. Thus, the start of irradiation of the radiation may be detected simply by changing the driving method. Therefore, there is no need to provide structures for detecting the start of irradiation of radiation, and there is no need to provide, for example, a design with dedicated TFT switches 4, or additional circuits or the like.

Seventh Exemplary Embodiment

Next, a seventh exemplary embodiment is described. In the present exemplary embodiment, structures and operations that are substantially the same as in the above exemplary embodiments are not described. The radiographic image detector 100 of the present exemplary embodiment has a method of detecting the start of irradiation of radiation that is different from the above exemplary embodiments. Therefore, the method of detecting the start of irradiation of radiation is described.

Figure 28:
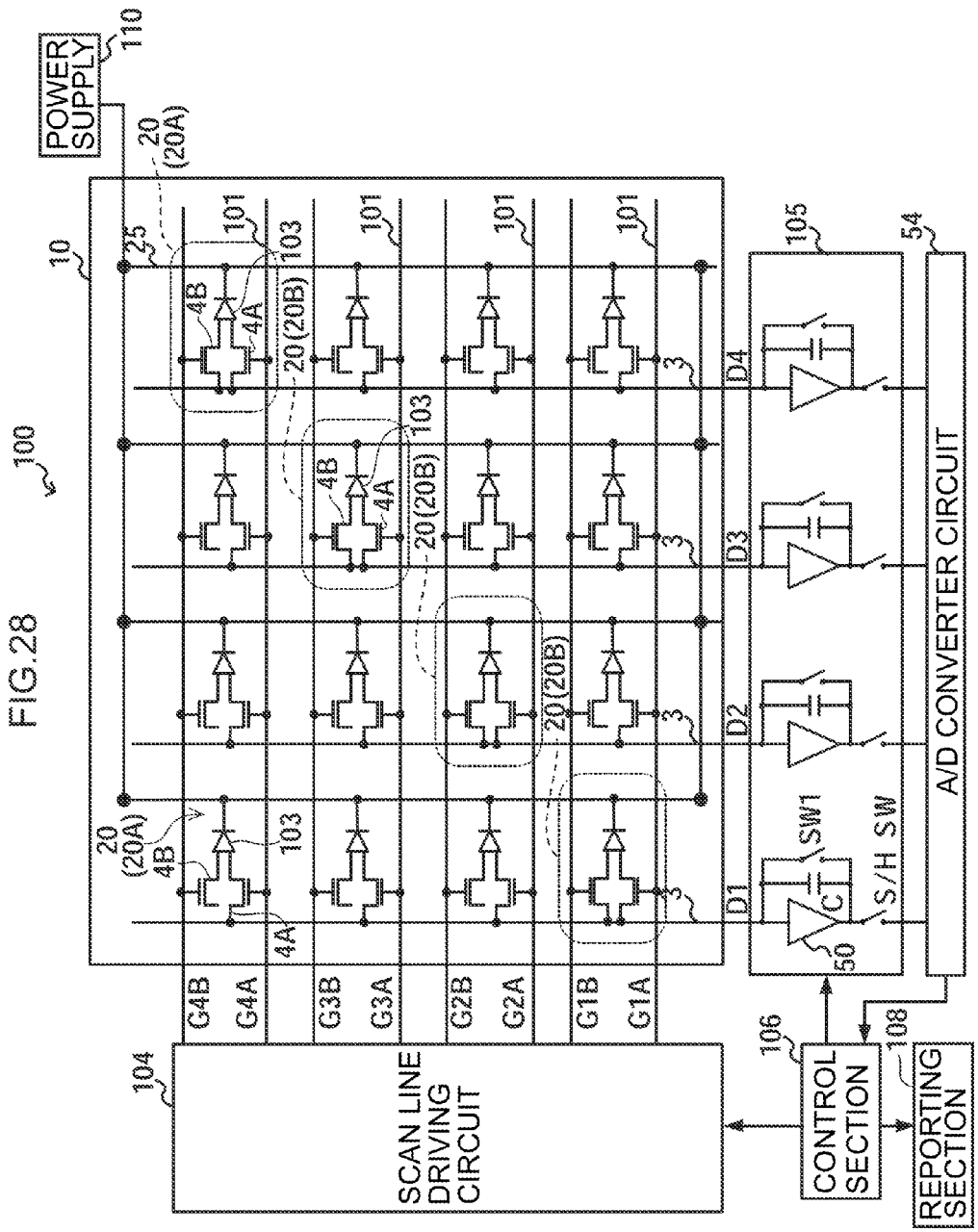
FIG. 28 is a structural diagram showing an example of overall structure of a radiographic image detector in accordance with a seventh exemplary embodiment.

In the radiographic image detector 100 of the present exemplary embodiment, each pixel 20 is provided with plural TFT switches 4. Control is performed to change which TFT switches 4 are used in a case in which the start of irradiation of radiation is detected or in a case in which an irradiation image is to be captured. FIG. 28 shows a structural diagram showing an example of overall structure of the radiographic image detector 100 of the present exemplary embodiment.

As shown in FIG. 28, each pixel 20 of the radiographic image detector 100 of the present exemplary embodiment is provided with two TFT switches 4 (4A and 4B). The TFT switches 4A are driven by driving signals that flow through the scan lines 101 (G1A, G2A, G3A and G4A), and are driven to the On state when charges for generating a radiographic image are to be read from the sensor portions 103. The TFT switches 4B are driven by driving signals that flow through others of the scan lines 101 (G1B, G2B, G3B and G4B), and are driven to the On state when charges are to be read from the sensor portions 103 when detecting for the start of irradiation of radiation. At the radiation image capturing pixels 20A, the TFT switches 4A are connected to the signal lines 3 but the TFT switches 4B are not connected to the signal lines 3. At the radiation detection pixels 20B, both the TFT switches 4A and the TFT switches 4B are connected to the signal lines 3.

Figure 29B:
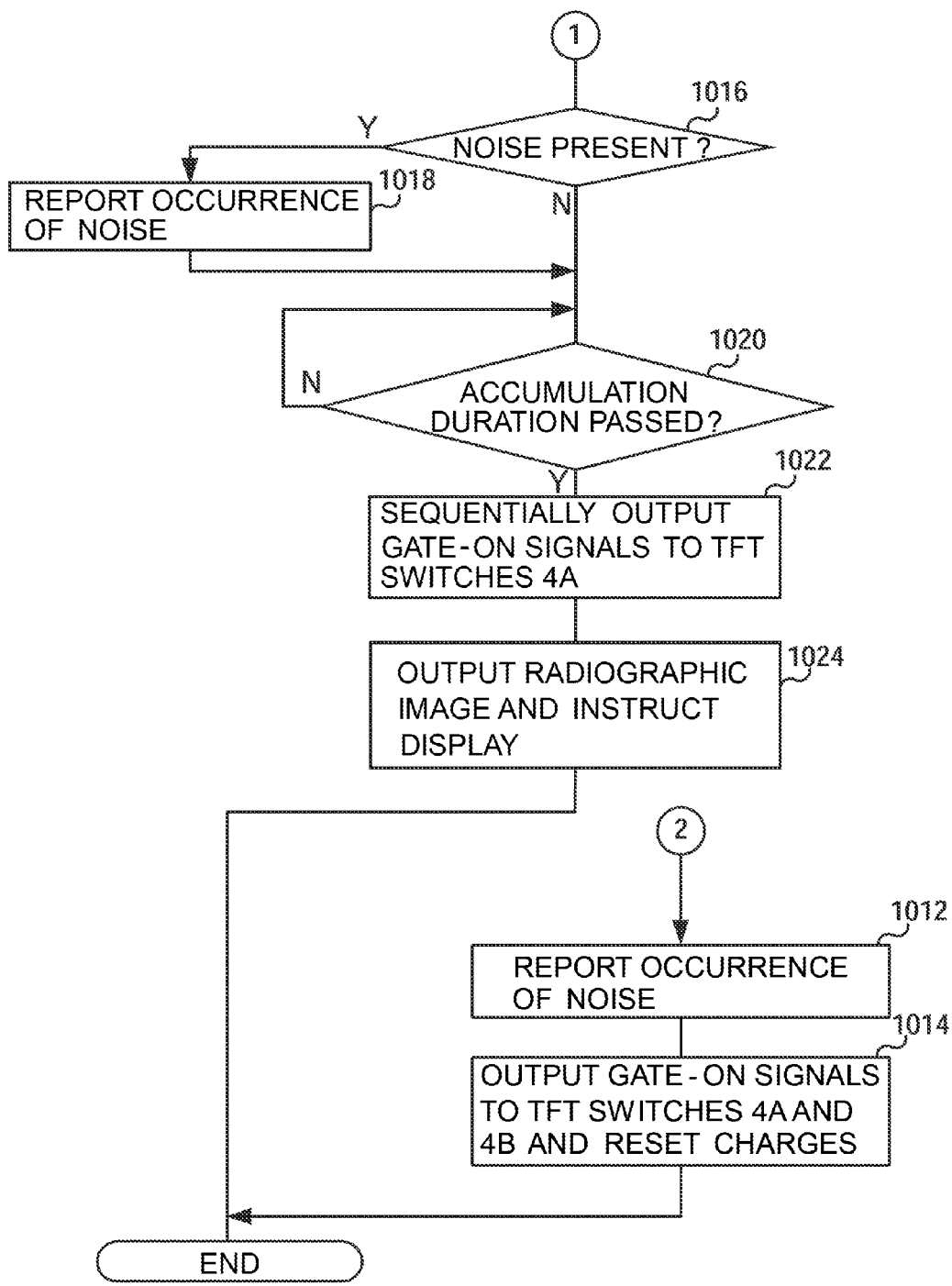

The image capture processing of the present exemplary embodiment is now described. The present exemplary embodiment includes steps (processing) substantially the same as in the image capture processing of the first exemplary embodiment (see FIG. 7). Therefore, steps (processing) that are substantially the same are denoted thus and details thereof are not described. FIGS. 29A and 29B show a flowchart of an example of overall image capture processing in the radiographic image detector 100 of the present exemplary embodiment.

In step 1000, the scan line driving circuit 104 is instructed to output driving signals for reset driving of the TFT switches 4A, and the scan line driving circuit 104 is instructed to output driving signals (gate-on signals) to the TFT switches 4B.

Thereafter, steps 1001 to 1024 correspond to steps 100 to 124, respectively, of the image capture processing of the first exemplary embodiment. Step 1001 corresponds to step 100 of the image capture processing of the first exemplary embodiment, starting the driving of the amplification circuits 50 (amplifiers 52) of the signal detection circuit 105 and continuously driving the same. Hence, charges are read out from the radiation detection pixels 20B by the TFT switches 4B, and electronic signals corresponding to the irradiation of radiation flow in the signal lines 3 and are sampled by the amplification circuits 50 (amplifiers 52). At the radiation image capturing pixels 20A, because the TFT switches 4B are not connected to the signal lines 3, electronic signals are not read out to the signal lines 3 by the TFT switches 4B, regardless of gate-on signals being applied to the TFT switches 4B.

Then, in step 1002, the control section 106 compares electronic signals according to the charges sampled by the amplification circuits 50 with a seventh threshold, and detects whether an irradiation of radiation has started from whether or not the electronic signals are at or above the seventh threshold. Note that the seventh threshold value may be found as a threshold for the start of irradiation of radiation by prior testing or the like.

If the electronic signals are below the seventh threshold, the result of the determination is negative and the control section 106 goes into the standby state. However, if the electronic signals are greater than or equal to the seventh exemplary embodiment, the start of irradiation of radiation is detected. Therefore, the result of the determination is affirmative and the control section 106 proceeds to step 1003. In step 1003, gate-off signals are outputted to the TFT switches 4A and the TFT switches 4B, and the accumulation of charges by the pixels 20 is started. After the start of the accumulation of charges, steps 1004 to 1018 for detecting noise are substantially the same as steps 104 to 118 of the first exemplary embodiment. The presence or absence, strength and duration of noise are detected on the basis of changes over time of electronic signals. Depending on the detection results, the detection results are displayed and a radiographic image is displayed. In the present exemplary embodiment, if a radiographic image is not to be displayed (if noise with a high strength and a long duration is detected), then in step 1014 gate-on signals are outputted to both the TFT switches 4A and the TFT switches 4B and the charges accumulated in the pixels 20 are reset.

Steps 1020 to 1024 for capturing a radiographic image carry out processing substantially the same as steps 120 to 124 of the first exemplary embodiment. When the accumulation duration has passed, the charges are sequentially read out from the pixels 20. At this time in the present exemplary embodiment, gate-on signals are outputted to the TFT switches 4A and electronic signals according to the accumulated charges are read out to the signal lines 3 by the TFT switches 4A. In the present exemplary embodiment, charges are read out from both the radiation image capturing pixels 20A and the radiation detection pixels 20B at this time. The control section 106 generates a radiographic image on the basis of the acquired electronic signals. The generated radiographic image is outputted to the control device 202 to be displayed, then the present processing ends.

In the present exemplary embodiment, the pixels 20 are equipped with the TFT switches 4A for radiographic image capture and the TFT switches 4B for radiation irradiation start detection. When the start of irradiation of radiation is being detected, the start of the irradiation of radiation is detected for on the basis of electronic signals that are outputted from the radiation detection pixels 20B to the signal lines 3 by the TFT switches 4B. When a radiographic image is being captured, electronic signals outputted to the signal lines 3 by the TFT switches 4A of the radiation image capturing pixels 20A and the radiation detection pixels 20B are acquired and the radiographic image is generated. Thus, when the start of irradiation of radiation is being detected for, signal strengths may be larger than in the case of using leakage currents described in the sixth exemplary embodiment hereabove. Therefore, the signal-to-noise ratio may be improved. Moreover, a radiation loss period from the start of the actual irradiation of radiation to the detection of the start of irradiation may be reduced. Consequently, a loss of charges due to reset driving may be disregarded. Furthermore, because the radiographic image may be generated by charges (electronic signals) read out from the radiation image capturing pixels 20A and the radiation detection pixels 20B, the radiation detection pixels 20B do not act as defect pixels, and image defects in the radiographic image may be suppressed.

The present exemplary embodiment has a structure in which the TFT switches 4A and TFT switches 4B are provided at all of the pixels 20, but this is not limiting. It is sufficient if the radiation detection pixels 20B are equipped with both the TFT switches 4 (4A and 4B). However, equipping all of the pixels 20 with the TFT switches 4A and the TFT switches 4B is preferable in regard to fabrication of the radiographic image detector 100 and the like.

Now, in the exemplary embodiments described above, detections of noise are performed by the control section 106 of the radiographic image detector 100 but this is not limiting. For example, the detections of noise may be performed by the control section 210 of the control device 202.

Further, in the exemplary embodiments described above, detections of noise are performed using respective threshold values, but this is not limiting. For example, detections may be based on waveforms of electronic signals, times between peaks of predetermined periods and the like. In the exemplary embodiments described above, signal analysis is performed by differentiation of the driving signals, differences from moving averages or the like, but this is not limiting. Other signal analysis processes may be performed. However, differentiation processing has high resolution. For example, even if a radiation irradiation timing and a noise generation timing overlap, they may be suitably distinguished. Therefore, differentiation processing is preferable.

The detection of the start of irradiation of radiation is not limited by the above exemplary embodiments, and structures are not particularly limited providing the start of irradiation of radiation is detected. For example, separate pixels 20 for radiation detection may be provided, or some of the radiation image capturing pixels 20A may be used. In the above exemplary embodiments, the detection is performed by comparison with a first threshold, but this is not limiting. Detection may be performed from whether or not predefined conditions, which are conditions for the start of the irradiation of radiation, are satisfied, and detection is not particularly limited.

In the above exemplary embodiments, cases in which radiographic images are displayed at the display section 212 of the control device 202 are described, but this is not limiting. For example, radiographic images may be displayed at an external display device or the like that is apart from the control device 202.

In the above exemplary embodiments, an indirect conversion system is described, but this is not limiting. A direct conversion system may be employed, in which radiation is directly converted to charges by a semiconductor layer and accumulated. In such a case, radiation detection elements in the direct conversion system generate charges when irradiated with radiation.

It will be clear that the structures, operations, and the like of the radiographic image detector 100 and the radiation detector 10 and the like described in the above exemplary embodiments are examples and may be modified in accordance with circumstances within a scope not departing from the spirit of the present invention.

The "radiation" of the present invention is not particularly limited by the present exemplary embodiments; x-rays, gamma rays and the like may be employed.

According to the first aspect of the present invention, there is provided a radiation image capturing device including: a plurality of pixels that are each provided with a sensor portion that generates a charge in accordance with an amount of radiation irradiated thereon, and a switching element that reads out the charge generated at the sensor portion and outputs the charge to a signal line; a detection unit that detects a start of irradiation if electronic signals corresponding to the charges generated at the sensor portions satisfy a pre-specified condition for irradiation detection; and a control unit that, after the start of an irradiation of radiation is detected by the detection unit, acquires electronic signals corresponding to the charges read out from the pixels, determines whether the acquired electronic signals include an electronic signal caused by noise, and, if an electronic signal caused by noise is included, controls a reporting unit so as to report the same.

According to the second aspect of the present invention, in the first aspect of the present invention, after the start of irradiation of radiation is detected by the detection unit, the control unit may detect a strength and a duration of the noise on the basis of the acquired electronic signals, a pre-specified condition for noise strength detection and a pre-specified condition for noise duration detection, and may determine whether or not to output a radiographic image on the basis of the detected strength and duration.

According to the third aspect of the present invention, in the first or second aspect of the present invention, the control unit may determine that a radiographic image is to be outputted if at least one of a low strength of the noise or a short duration of the noise is detected.

According to the fourth aspect of the present invention, in any one of the first to third aspects of the present invention, the control unit may determine that a radiographic image is not to be output if it is detected that the strength of the noise is high and the duration of the noise is long.

According to the fifth aspect of the present invention, in any one of the first to fourth aspects of the present invention, the control unit may acquire the electronic signals corresponding to the charges from each of pre-specified regions which are pre-specified according to the plurality of pixels, and may determine whether the acquired electronic signals include an electronic signal caused by noise, for each of the pre-specified regions.

According to the sixth aspect of the present invention, in the fifth aspect of the present invention, the control unit may report at least one of the pre-specified regions for which it has been determined that an electronic signal caused by noise is included.

According to the seventh aspect of the present invention, in the fifth or sixth aspect of the present invention, the control unit may determine whether or not to output a radiographic image on the basis of a location of at least one of the pre-specified regions for which it has been determined that an electronic signal caused by noise is included.

According to the eighth aspect of the present invention, in the seventh aspect of the present invention, the control unit may determine that the radiographic image is not to be output if the location of the at least one of the pre-specified regions, for which it has been determined that an electronic signal caused by noise is included, is a pre-specified location which is pre-specified as central relative to all the regions.

According to the ninth aspect of the present invention, in any one of the first to eighth aspects of the present invention, on the basis of changes over time of the acquired electronic signals, the control unit may determine that an electronic signal caused by noise is included if at least one of the acquired electronic signals exceeds a threshold for noise detection.

According to the tenth aspect of the present invention, in the ninth aspect of the present invention, on the basis of electronic signals that are differentiated with respect to changes over time of the acquired electronic signals, the control unit may determine that an electronic signal caused by noise is included if a differentiated electronic signal exceeds a threshold for noise detection.

According to the eleventh aspect of the present invention, in the ninth aspect of the present invention, on the basis of changes over time of the acquired electronic signals, the control unit may calculate a time moving average and, on the basis of differences of the electronic signals at a time of determination from the calculated time moving average, the control unit may determine that an electronic signal caused by noise is included if a difference exceeds a threshold for noise detection.

According to the twelfth aspect of the present invention, in any one of the second to eleventh aspects of the present invention, the control unit may detect the strength of the noise by comparing the acquired electronic signals with a threshold for strength detection.

According to the thirteenth aspect of the present invention, in any one of the second to twelfth aspects of the present invention, the control unit may detect the duration of the noise on the basis of a number of times the acquired electronic signals reach a threshold for duration detection.

According to the fourteenth aspect of the present invention, in any one of the first to thirteenth aspects of the present invention, the reporting unit may be provided at a radiographic image detector that includes the plurality of pixels.

According to the fifteenth aspect of the present invention, in any one of the first to fourteenth aspects of the present invention, the reporting unit may be provided externally to a radiographic image detector that includes the plurality of pixels.

According to the sixteenth aspect of the present invention, in any one of the first to fifteenth of the present invention, the plurality of pixels may include radiation image capturing pixels and radiation detection pixels; the detection unit may detect the start of irradiation of radiation on the basis of electronic signals corresponding to charges output from the radiation detection pixels; and the control unit may acquire electronic signals corresponding to charges read out from the radiation detection pixels.

According to the seventeenth aspect of the present invention, in the sixteenth aspect of the present invention, the switching elements of the radiation image capturing pixels may output charges to the signal lines in accordance with control signals; and the radiation detection pixels may output charges to the signal lines regardless of the control signals.

According to the eighteenth aspect of the present invention, in the sixteenth aspect of the present invention, each of the radiation detection pixels may include a switching element for radiation image capturing that is driven in accordance with a control signal flowing through a first scan line, and a switching element for radiation detection that is driven in accordance with a control signal flowing through a second scan line, the detection unit may detect the start of irradiation of radiation on the basis of electronic signals corresponding to charges that are read out by driving of the switching elements for radiation detection, and the control unit may acquire electronic signals corresponding to charges that are read out from the radiation image capturing pixels and electronic signals corresponding to charges that are read out by driving of the switching elements for radiation image capturing of the radiation detection pixels.

According to the nineteenth aspect of the present invention, in the eighteenth aspect of the present invention, each of the radiation image capturing pixels may include a switching element for radiation image capturing and a switching element for radiation detection, and the switching element for radiation detection is not connected to the signal line.

According to the twentieth aspect of the present invention, in any one of the first to fifteenth aspects of the present invention may further include: bias lines that supply a bias voltage applied from a bias power supply to the sensor portions of the plurality of pixels; and a charge detection unit that detects charges flowing in the bias lines, wherein the detection unit may detect the start of an irradiation radiation on the basis of a change in charges detected by the charge detection unit.

According to the twenty-first aspect of the present invention, in the twentieth aspect of the present invention, in a detection period during which the detection unit can detect the start of irradiation of radiation, the switching elements may be in an off state.

According to the twenty-second aspect of the present invention, in the twenty-first aspect of the present invention, at intervals of a predetermined duration in the detection period, the detection for the start of irradiation of radiation may be suspended, the switching elements may be put into an on state, charges generated at the sensor portions may be read out and outputted to the signal lines, then the switching elements may be put into an off state, and the detection for the start of irradiation of radiation may be resumed.

According to the twenty-third aspect of the present invention, in any one of the first to twenty-second aspects of the present invention, the pre-specified condition for irradiation detection may be a pre-specified condition which is pre-specified based on a threshold for irradiation detection.

According to the twenty-fourth aspect of the present invention, there is provided a radiation image capturing system including: a radiation irradiation device; and the radiation image capturing device according to one of the first to twenty-third aspects that captures a radiographic image according to radiation irradiated from the radiation irradiation device.

According to the twenty-fifth aspect of the present invention, there is provided a radiation image capturing device control method including, when a radiographic image is being captured by a radiation image capturing device that includes a plurality of pixels that are each provided with a sensor portion that generates a charge in accordance with radiation irradiated thereon, and a switching element that reads out the charge generated at the sensor portion and outputs the charge to a signal line, detecting a start of irradiation of radiation if electronic signals corresponding to charges generated in the sensor portions satisfy a pre-specified condition for irradiation detection; after the start of irradiation of radiation is detected by the detecting, acquiring electronic signals corresponding to charges read out from the pixels; determining whether the acquired electronic signals include an electronic signal caused by noise; and, if an electronic signal caused by noise is included, controlling a reporting unit so as to report the same.

According to the twenty-sixth aspect of the present invention, there is provided a non-transitory computer readable medium storing a radiation image capturing device control program that causes a computer to execute a process for functioning as a control unit of a radiation image capturing device, the radiation image capturing device including: a plurality of pixels that are each provided with a sensor portion that generates a charge in accordance with radiation irradiated thereon, and a switching element that reads out the charge generated at the sensor portion and outputs the charge to a signal line; a detection unit that detects a start of irradiation of radiation if electronic signals corresponding to charges generated in the sensor portions satisfy a pre-specified condition for irradiation detection; and the control unit, which, after the start of irradiation of radiation is detected by the detection unit, acquires electronic signals corresponding to charges read out from the pixels, determines whether the acquired electronic signals include an electronic signal caused by noise, and, if an electronic signal caused by noise is included, controls a reporting unit so as to report the same.

As described above, the presence/absence of noise when a radiographic image is being captured may be suitably detected and reported.

Embodiments of the present invention are described above, but the present invention is not limited to the embodiments as will be clear to those skilled in the art.

What is claimed is:

1. A radiation image capturing device comprising:
a plurality of pixels that are each provided with a sensor portion, that generates a charge in accordance with an amount of radiation irradiated thereon and accumulates the generated charge, and with a switching element that reads out the charge generated and accumulated at the sensor portion and outputs the charge to a signal line;
a detection unit that detects a start of irradiation in a case in which electronic signals corresponding to the charges generated at the sensor portions satisfy a pre-specified condition for irradiation detection; and
a control unit that, after the start of irradiation of radiation is detected by the detection unit, acquires electronic signals corresponding to the charges read out from the pixels for each of pre-specified regions, determines whether the acquired electronic signals include an electronic signal caused by noise for each of the pre-specified regions, and, in a case in which an electronic signal caused by noise is included, performs control that includes associating a radiation image with information relating to a pre-specified region in which it is determined that an electronic signal caused by noise is included, and storing thereof at at least one of within or outside the radiation image capturing device.

2. The radiation image capturing device according to claim 1, further comprising an image processing unit that performs pre-determined image processing that removes the noise that has been determined by the control unit with respect to the radiation image, and
wherein the control unit further performs control that includes associating at least one of a radiation image after the image processing by the image processing unit or a radiation image before the image processing by the image processing unit, with the information relating to the pre-specified region in which it is determined that the electronic signal caused by noise is included, and storing thereof.

3. The radiation image capturing device according to claim 2, further comprising a display unit that displays the radiation image after the image processing by the image processing unit.

4. The radiation image capturing device according to claim 2, wherein the control unit outputs the radiation image in a case in which a number of pre-specified regions, determined to include an electronic signal caused by noise, is less than a pre-specified threshold value.

5. The radiation image capturing device according to claim 4, wherein the control unit outputs an instruction to re-capture a radiation image without outputting the radiation image in a case in which a number of pre-specified regions, determined to include an electronic signal caused by noise, is greater than or equal to the pre-specified threshold value.

6. The radiation image capturing device according to claim 1, further comprising a setting unit that sets to display the radiation image at a display unit regardless of a determination result of presence or absence of noise by the control unit, and wherein the control unit outputs the radiation image to the display unit in a case in which the radiation image is to be displayed regardless of the determination result of presence or absence of noise based on the setting of the setting unit.

7. The radiation image capturing device according to claim 1, wherein the control unit determines whether or not the radiation image is output based on a number and a location of pre-specified regions determined to include an electronic signal caused by noise.

8. The radiation image capturing device according to claim 1, wherein the control unit outputs an instruction to stop irradiation of radiation to a radiation irradiation device in a case in which a strength of noise is detected based on the acquired electronic signal and a condition for detecting a strength of noise, and it is detected that the strength of noise is stronger than a pre-specified strength, and in a case in which an occurrence period of noise is detected based on the acquired electronic signal and a condition for detecting an occurrence period of noise, and it is detected that the occurrence period of noise is longer than a pre-specified length.

9. The radiation image capturing device according to claim 1, wherein the control unit determines whether the acquired electronic signal includes an electronic signal caused by noise based on a duration of a peak of the acquired electronic signal.

10. The radiation image capturing device according to claim 1, further comprising an amplifier that samples electronic signals corresponding to the charges read out from the sensor portion, and wherein the control unit acquires the sampled electronic signals by the amplifier, and, in a case in which the radiation image is not to be output based on a determination result, for which it is determined whether or not the sampled electronic signals include an electronic signal caused by noise, the control unit resets charges accumulated at the sensor portion and then starts to drive the amplifier.

11. The radiation image capturing device according to claim 1, wherein a control program of the radiation image capturing device, that causes a computer to function as the control unit, is supplied outside the radiation image capturing device.

12. A radiation image capturing system comprising:
a radiation irradiation device; and
the radiation image capturing device according to claim 1, which captures a radiographic image according to radiation output from the radiation irradiation device.

13. A non-transitory computer readable medium storing a radiation image capturing device control program that causes a computer to function as the control unit of the radiation image capturing device according to claim 1.

14. A radiation image capturing device control method, comprising:
when capturing a radiation image, by a radiation image capturing device that comprises a plurality of pixels that are each provided with a sensor portion that generates a charge in accordance with an amount of radiation irradiated thereon and accumulates the generated charge, and with a switching element that reads out the charge generated and accumulated at the sensor portion and outputs the charge to a signal line:
detecting a start of irradiation in a case in which electronic signals corresponding to the charges generated at the sensor portions satisfy a pre-specified condition for irradiation detection; and
performing control that includes, after the start of irradiation of radiation is detected, acquiring electronic signals corresponding to the charges read out from the pixels for each of pre-specified regions, determining whether the acquired electronic signals include an electronic signal caused by noise for each of the pre-specified regions, and, in a case in which an electronic signal caused by noise is included, associating a radiation image and information relating to a pre-specified region in which it is determined that an electronic signal caused by noise is included, and storing thereof at at least one of within or outside the radiation image capturing device.

* * * * *